(12) United States Patent
Kambe et al.

(10) Patent No.: US 10,703,773 B2
(45) Date of Patent: Jul. 7, 2020

(54) GLYCOSYL HESPERETIN AND PROCESS FOR PRODUCING THE SAME AND USES THEREOF

(71) Applicant: Hayashibara Co. Ltd., Okayama-shi, Okayama (JP)

(72) Inventors: Mitsuyuki Kambe, Okayama (JP); Koichi Nishi, Okayama (JP); Akira Kawashima, Okayama (JP); Akiko Yasuda, Okayama (JP); Hitoshi Mitsuzumi, Okayama (JP); Toshio Ariyasu, Okayama (JP)

(73) Assignee: HAYASHIBARA CO. LTD., Okayama (JP)

( * ) Notice: Subject to any disclaimer, the term of this patent is extended or adjusted under 35 U.S.C. 154(b) by 114 days.

(21) Appl. No.: 15/122,708

(22) PCT Filed: Mar. 3, 2015

(86) PCT No.: PCT/JP2015/056230
§ 371 (c)(1),
(2) Date: Aug. 31, 2016

(87) PCT Pub. No.: WO2015/133483
PCT Pub. Date: Sep. 11, 2015

(65) Prior Publication Data
US 2017/0081354 A1    Mar. 23, 2017

(30) Foreign Application Priority Data

Mar. 3, 2014 (JP) ................................ 2014-041066
Dec. 26, 2014 (JP) ................................ 2014-266504

(51) Int. Cl.
| | | |
|---|---|---|
| C07G 3/00 | (2006.01) | |
| C07H 17/00 | (2006.01) | |
| C07H 17/07 | (2006.01) | |
| A61Q 19/00 | (2006.01) | |
| A61K 31/7048 | (2006.01) | |
| A23L 27/00 | (2016.01) | |
| A23L 27/20 | (2016.01) | |
| A23L 33/10 | (2016.01) | |
| A23L 33/15 | (2016.01) | |
| A61K 8/60 | (2006.01) | |
| C12P 19/60 | (2006.01) | |
| A23L 2/52 | (2006.01) | |
| C12P 19/18 | (2006.01) | |
| C12P 19/14 | (2006.01) | |

(52) U.S. Cl.
CPC .............. *C07H 17/07* (2013.01); *A23L 2/52* (2013.01); *A23L 27/2052* (2016.08); *A23L 27/84* (2016.08); *A23L 33/10* (2016.08); *A23L 33/15* (2016.08); *A61K 8/602* (2013.01); *A61K 31/7048* (2013.01); *A61Q 19/00* (2013.01); *C12P 19/14* (2013.01); *C12P 19/18* (2013.01);

*C12P 19/60* (2013.01); *A23V 2002/00* (2013.01); *A61K 2800/10* (2013.01)

(58) Field of Classification Search
None
See application file for complete search history.

(56) References Cited

U.S. PATENT DOCUMENTS

| | | | |
|---|---|---|---|
| 5,627,157 A | 5/1997 | Hijiya et al. | |
| 5,652,124 A * | 7/1997 | Hiyiya et al. | ................... 435/78 |
| 5,885,969 A | 3/1999 | Miyake et al. | |
| 6,048,712 A | 4/2000 | Miyake et al. | |
| 8,399,034 B2 * | 3/2013 | Koike et al. | ................... 426/74 |

FOREIGN PATENT DOCUMENTS

| | | |
|---|---|---|
| JP | 3-7593 A | 1/1991 |
| JP | 10-70994 A | 3/1998 |
| JP | 10-323196 A | 12/1998 |
| JP | 11-346792 A | 12/1999 |
| JP | 3060227 B2 | 4/2000 |
| JP | 3833811 B2 | 7/2006 |
| JP | 2007-39349 A | 2/2007 |
| JP | 2011-126849 A | 6/2011 |
| WO | 2013018779 A1 | 2/2013 |
| WO | 2016/027837 A1 | 2/2016 |

OTHER PUBLICATIONS

Yamamoto et al. (2008), vol. 54, pp. 95-98.*
Winkler et al. Food and Chemical Toxicology (2006), vol. 44, pp. 2003-2007.*
Mancilha et al. Biotechnol. Prog. (2003), vol. 19, pp. 1837-1841.*
Lee et al. Journal of Food Science (1986), vol. 51, pp. 1075-1076.*
Grotheer et al. "Sulfites: separating fact from fiction." Department of Family, Youth, and Community Sciences, University of Florida (2005).*
Talebnia et al. "Citrus waste saccharification," (2008) BioResources 3(1), pp. 108-122.*
Kometani, T. et al., SynthesIs of Neohesperidin Glycosides and Naringin Glycosides by Cyclodextrin Glucanotransferase from an Alkalophilic *Bacillus* Species, BioscIence, Biotechnology, and Biochemistry, 60(4):645-649 (1996).
Li et al., Bulk Chemical Data Sheet Manual for Shipment by Water and Terminal, Tongji University Press, May 31, 2012, with English Excerpt Translation of p. 234.

* cited by examiner

*Primary Examiner* — Patrick T Lewis
(74) *Attorney, Agent, or Firm* — Browdy and Neimark, PLLC

(57) ABSTRACT

The present invention aims to provide a novel glycosyl hesperetin, which is significantly reduced in miscellaneous tastes characteristic of conventional products containing glycosyl hesperetin, and a method for producing the same and uses thereof; and the objects are solved by providing a glycosyl hesperetin which comprises glycosyl hesperetin in an amount of 90% or more by mass but less than 100% by mass, on a dry solid basis, but it does not substantially contain furfural, and a method for producing the same and uses thereof.

4 Claims, No Drawings

GLYCOSYL HESPERETIN AND PROCESS FOR PRODUCING THE SAME AND USES THEREOF

TECHNICAL FIELD

The present invention relates to a novel glycosyl hesperetin, and more particularly, to a glycosyl hesperetin that is significantly reduced in miscellaneous tastes, and its production and uses. Although the details will be described later, the term glycosyl hesperetin as referred to as in the specification means compounds in general, composed of hesperetin coupled with a saccharide(s) (called "compounds having the hesperetin structure", hereinafter); hesperidin, 7-O-β-glucosyl hesperetin having a partial structure of hesperidin, in which the rhamnose residue as a constituent of rutinose in hesperidin has been released therefrom, and α-glycosyl hesperidins, in which an equimolar or more saccharides such as D-glucose, ID-fructose, and D-galactose are bound to hesperidin in α-bonding.

BACKGROUND ART

It is known that, among vitamins, vitamin P relates to the physiological functions of vitamin C in living bodies, for example, it relates to the hydroxylation reaction of proline and lysine required for the synthesis of collagen as a main ingredient of biological connective tissues, as well as to the redox reaction of reducing $Fe^{+++}$ in cytochrome C into $Fe^{++}$ and to the immuno-enhancing effect of leukocytosis; and plays an important role in the maintenance and promotion of the health of living bodies.

Hesperidin, also known as vitamin P, is a compound represented by the following Chemical Formula 1 with the hesperetin structure, where rutinose composed of rhamnose and glucose binds to hesperetin, and it is a form of flavonoid contained abundantly in pericarps of citrus fruits; further, it has been known and used since a long time ago as vitamin P having physiological functions of reinforcing capillaries, preventing bleeding, and regulating blood pressure; and extensively used, for example, in food products, cosmetics, pharmaceuticals, etc.

In addition to the use of hesperidin as a vitamin P-enriched agent as a mere nutrient, hesperidin, in view of its chemical structure and physiological functions, can be incorporated alone or in combination with other vitamins into food products as an antioxidant, stabilizer, quality-improving agent, ultraviolet-absorbing agent, etc; pharmaceuticals such as prophylactic and therapeutic agents, i.e., agents for hesperidin-susceptive diseases such as hesperidin-susceptive viral diseases, bacterial diseases, circulatory diseases, and malignant tumors; and even into cosmetics such as skin-beautifying agents, skin-whitening agents, and anti-aging agents as a stabilizer, antioxidant, ultraviolet-absorbing agent, and melanin-formation inhibitory agent. Thus, hesperidin is used quite extensively.

However, since hesperidin hardly dissolves in water at a mere concentration of about one gram in 50 L of water (or about 0.002 w/v %) at ambient temperature, it has a severe difficulty in use.

As a means for improving the above problem, for example, Patent Literature 1 discloses α-glycosyl hesperidin, prepared by allowing a saccharide-transferring enzyme (or glycosyltransferase) to act on a solution containing hesperidin and a partial starch hydrolyzate, having a relatively-high water solubility, and being easily hydrolyzed in vivo to exert the physiological functions inherent to hesperidin without fear of inducing any toxicity, and a method for producing the same.

As a representative example of α-glycosyl hesperidin, α-glucosyl hesperidin, known as an enzyme-treated hesperidin, saccharide-transferred/glycosyl hesperidin, water-soluble hesperidin, or saccharide-transferred/glycosyl vitamin P, is a compound shown in the following Chemical Formula 2, wherein one molar glucose is bound to the glucose in the rutinose structure of hesperidin via α-bonding, and it is commercialized as a product containing the same as a main ingredient, for example, "HAYASHIBARA HESPERIDIN® S", a product name of a glucosyl hesperidin, commercialized by Hayashibara Co., Ltd., Okayama, Japan.

Chemical Formula 1

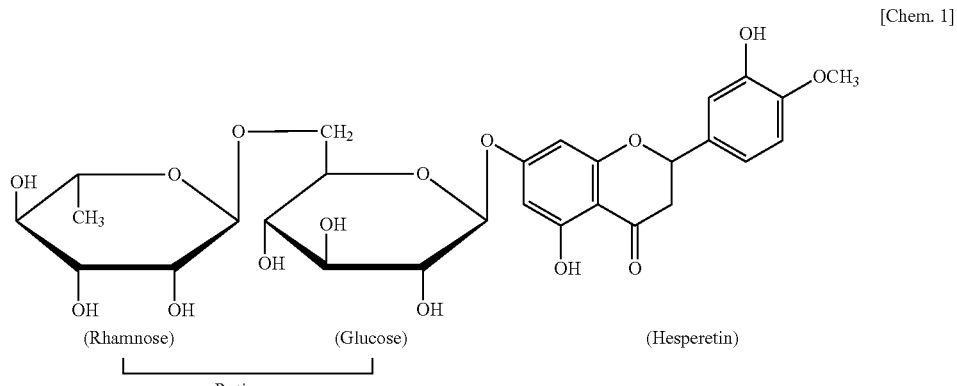

Hesperidin (Chemical Formula 1)

Chemical Formula 2

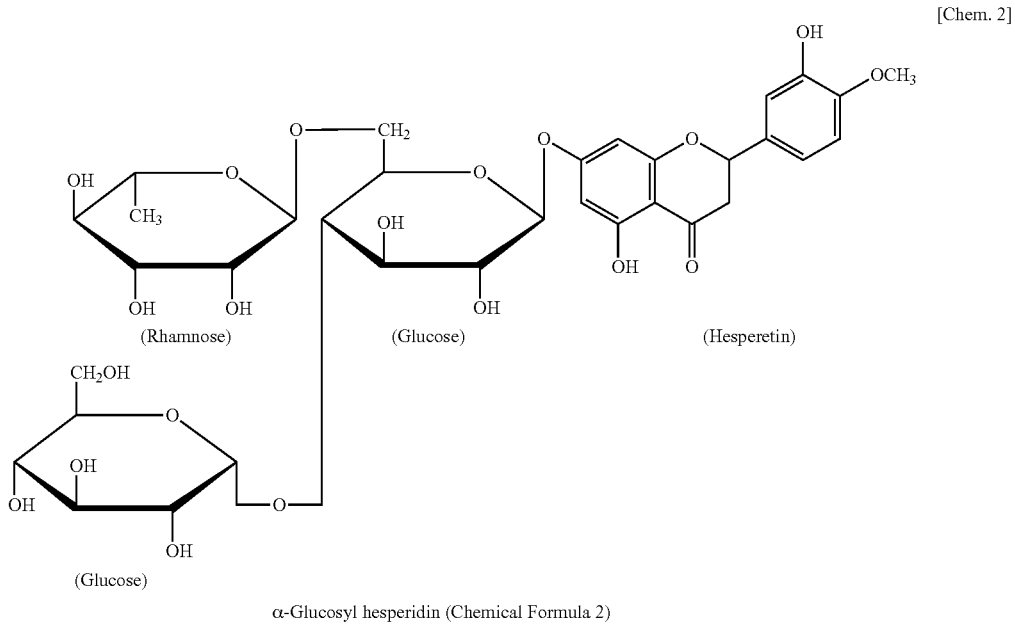

α-Glucosyl hesperidin (Chemical Formula 2)

It is known that conventional products, containing α-glycosyl hesperidin, contain concomitant hesperidin known as a causative production material for reducing the water solubility of α-glycosyl hesperidin; and, as a trial to improve the above reduction, a conversion of hesperidin into 7-O-β-glucosyl hesperetin, as shown in the following Chemical Formula 3, which is obtainable by releasing the rhamnose residue that constitutes the rutinose structure of hesperidin and has a distinctly-higher water solubility than hesperidin. For example, Patent Literature 2 discloses a method for producing an α-glycosyl hesperidin high content product with an improved water solubility by allowing α-L-rhamnosidase (EC 3. 2. 1. 40) to act on a solution containing hesperidin along with α-glucosyl hesperidin at a relatively high concentration to convert hesperidin into 7-O-β-glucosyl hesperetin and to reduce the content of the remaining hesperidin.

Chemical Formula 3

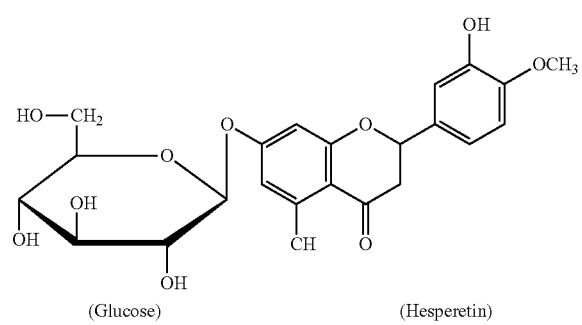

7-o-β-Glucosyl hesperitin (Chemical Formula 3)

Products containing glycosyl hesperetins, i.e., what are called glycosyl hesperetins such as conventional hesperidin, α-glucosyl hesperetin, and 7-O-β-glucosyl hesperetin (may be simply called "conventional products", hereinafter), have a specific bitterness (including roughness, harshness, or astringency) and an unfavorable aftertaste, i.e., a miscellaneous taste; there is disclosed, for example, in Patent Literature 3, a method of adding malic acid to beverages containing α-glycosyl hesperidin, i.e., glycosyl hesperidin, also known as a water-soluble hesperidin, as a method of improving the above defect.

However, even now, there has not yet been provided any glycosyl hesperetin product, whose miscellaneous tastes characteristic of conventional products have been improved to a fully satisfactory level.

PRIOR ART LITERATURES

Patent Literatures

Patent Literature 1: Registered Japanese Patent No. 3060227
Patent Literature 2: Registered Japanese Patent No. 3833811
Patent Literature 3: Japanese Patent Kokai No 2011-126849

DISCLOSURE OF INVENTION

Object of the Invention

The present invention, which was made to overcome the above defect, aims to provide an α-glycosyl hesperetin that is significantly reduced in miscellaneous tastes compared to conventional products, and its production and uses.

Means to Attain the Object

The present inventors focused on the miscellaneous tastes as a defect of conventional products and eagerly made research efforts with an aim to overcome the defect: The present inventors made an assumption that there must exist a causative substance(s) of the miscellaneous tastes of conventional products, which is(are) inherently contained in some production materials of the products (may be simply called "a causative substance(s) of the miscellaneous tastes", hereinafter) or such causative substance(s) is(are) formed during their production steps. Under the above assumption, the present inventors repeatedly made various studies on means for reducing the miscellaneous tastes of conventional products and newly found a glycosyl hesperetin whose miscellaneous tastes are significantly reduced compared to conventional products, when a reducing agent(s) is (are) coexisted in any of their production steps. Further, the present inventors newly found that such a novel glycosyl hesperetin is distinctly reduced in coloration and odor compared to conventional products. In addition, the present inventors compared in detail the features of the novel glycosyl hesperetin thus obtained with those of conventional products and found the followings: (A) They both are glycosyl hesperetin-based products but are different in the content of furfural, i.e., an aromatic aldehyde as a trace ingredient, or 2-furancarboxyaldehyde as an IUPAC Name; and (B) the novel glycosyl hesperetin with a significantly reduced in miscellaneous tastes of the present invention has a significantly-reduced furfural content compared to conventional products, and in other word this means that the one with a significantly-reduced furfural content is a glycosyl hesperetin that is significantly reduced in miscellaneous tastes compared to conventional products Based on these findings, the present inventors newly found that the furfural content could surely be made an index for obtaining a glycosyl hesperetin that is significantly reduced in miscellaneous tastes.

On the basis of the above series of findings, the present inventors accomplished the present invention in such a manner of focusing on the content of furfural, as an index for obtaining a glycosyl hesperetin that is significantly reduced in miscellaneous tastes as a defect of conventional products, contained in such a glycosyl hesperetin; and obtaining a desired glycosyl hesperetin, which is significantly reduced in miscellaneous tastes compared to conventional products, by using a reducing agent in any one of their production steps as a means for obtaining such a glycosyl hesperetin that is significantly reduced in furfural content.

The present invention solves the above objects by providing a glycosyl hesperetin which substantially does not contain furfural. The term "substantially does not contain furfural" as referred to as in the specification means that the content of furfural in the glycosyl hesperetin is in a significantly low level compared to conventional products. Concretely speaking, it means that the furfural content level is usually less than 200 ppb, where one ppb means billionth, preferably less than 100 ppb, more preferably less than 50 ppb, furthermore preferably less than 30 ppb, furthermore less than 20 ppb, particularly preferably less than 15 ppb, and most preferably less than 10 ppb, when determined with the later described analytical method using a gas chromatograph mass spectrometry (abbreviated as "GC/MS analyzer", hereinafter) shown in the item "(1) Furfural content" in the later described. Experiment 1. Among the glycosyl hesperetins according to the present invention, those which have a furfural content reduced to a level up to below the detection limit of GC/MS analyzer are distinctly-high-quality glycosyl hesperetins whose miscellaneous tastes are significantly reduced compared to conventional products and also whose colorations are distinctly reduced. Putting aside the use of the glycosyl hesperetin of the present invention in the fields of pharmaceuticals, precision apparatuses, etc., glycosyl hesperetin with a highest purity should not necessarily be required when used in the fields of food products, preferences, cosmetics, industrial feedstock/materials, feeds, baits, clothes, sundries including commodities, or plastic products; meaning that glycosyl hesperetin should neither necessarily be the one whose furfural content is reduced to a level below its detection limit nor be the one free from furfural. Thus, the glycosyl hesperetin of the present invention include those which substantially do not contain furfural or those which contain furfural in a significantly lesser level compared to conventional products or in an undetectable level, as long as they attain the desired objects of the present invention.

The present invention solves the aforesaid another object by providing a method for producing glycosyl hesperetin, which comprises the steps of (a) preparing an aqueous solution containing hesperidin and a partial starch hydrolyzate, (b) allowing a saccharide-transferring enzyme to act on the aqueous solution to form a glycosyl hesperetin containing α-glucosyl hesperidin, and (c) collecting the formed glycosyl hesperetin, wherein one or more of the steps (a) to (c) are effected in the presence of a reducing agent, or a reducing agent(s) is (are) added to a starting material(s) used before practicing one or more of the steps (a) to (c) and/or added to the resulting product(s) in any of these step(s).

Further, the present invention solves the aforesaid another object by providing food products, preferences, cosmetics, pharmaceuticals, quasi-drugs, chemicals, industrial feedstock/materials, feeds, baits, clothes, sundries including commodities, or plastic products, all of which contain the glycosyl hesperetin of the present invention.

The present invention also solves the aforesaid another object by providing a method for reducing miscellaneous tastes of a product containing glycosyl hesperetin, which contains a step of allowing the product to contact with a reducing agent.

Effect of the Invention

Unlike conventional products, the glycosyl hesperetin of the present invention has an outstanding feature of being significantly reduced in miscellaneous tastes. According to the method for producing glycosyl hesperetin of the present invention or the method for reducing the miscellaneous tastes of products containing glycosyl hesperetin of the present invention, there can be exerted practical benefits of providing glycosyl hesperetin that is significantly reduced in miscellaneous tastes compared to conventional products on an industrial scale, stably, and in a relatively high yield, as well as easily and in a lesser cost. Thus, the glycosyl hesperetin of the present invention can be preferably used in articles/goods/products in which conventional products could not hardly be used or which would have troublesome due to their miscellaneous tastes alone or along with their colorations, or even due to their odors. Since the glycosyl hesperetin of the present invention, compared to conventional products, is significantly reduced in miscellaneous tastes, as well as being distinctly reduced in coloration and odor, it exerts an advantageously practical benefit in that it provides high-quality products even when they are produced through heating steps.

MODE FOR CARRYING OUT THE INVENTION

The following explain the preferred embodiments of the present invention, just merely exemplify the preferred embodiments for practicing the present invention, and should never restrict the present invention.

The glycosyl hesperetin of the present invention has in common with conventional products in that they are mainly composed of glycosyl hesperetin, but the former is a novel glycosyl hesperetin that is significantly reduced in miscellaneous tastes, compared to the latter.

The term "glycosyl hesperetin" as referred to as in the present invention means a composition which contains as a main ingredient(s) either or both of (1) α-glycosyl hesperidin (α-glucosyl hesperidin, etc.) and (2) hesperidin and 7-O-β-glucosyl hesperetin, i.e., a mixture of glycosyl hesperetins; and which further contains (3) flavonoids such as narirutin, diosmin, neoponcirin, and glucosyl narirutin, and (4) trace ingredients such as salts. The total percentage (% by mass) of the above ingredients (1) and (2) in the glycosyl hesperetin of the present invention (simply called "glycosyl hesperetin content", unless specified otherwise, hereinafter) is usually, on a dry solid basis (d.s.b.), at least 90% by mass but less than 100% by mass, preferably at least 93% by mass but less than 100% by mass, more preferably at least 95% by mass but less than 100% by mass, more further preferably at least 97% by mass but less than 100% by mass, and further at least 98% by mass but less than 100% by mass (throughout the specification, "% by mass" is abbreviated as "%", if not specified otherwise).

Putting aside the use of the glycosyl hesperetin of the present invention in the fields of pharmaceuticals, precision apparatuses, etc., when it is used in the fields of food products, preferences, cosmetics, industrial feedstock/materials, feeds, baits, clothes, sundries including commodities, or plastic products, in which glycosyl hesperetin with a highest purity should not substantially be required or even the one with a relatively low purity does not substantially cause any specific troublesome, the upper limit of the glycosyl hesperetin of the present invention is usually 99%, d.s.b., which easily affords the supply on an industrial scale and at a lesser cost; 98%, d.s.b., which affords the supply at a lesser cost; and even a low level of up to 97% or lower, d.s.b., which affords the supply at a more lesser cost, while considering the forms of final products and enabling the supply of the products at a lesser cost. However, in the case of the content, d.s.b., of glycosyl hesperetin in the glycosyl hesperetin of the present invention is relatively low, it should inevitably be required in a larger amount than in the case of using the one with a higher content of glycosyl hesperetin, resulting in a laborious handling and an unfavorable handleability. To avoid such defect, the lower limit of the glycosyl hesperetin content is usually at least 90%, preferably at least 93%, more preferably at least 95%, and further more preferably at least 97%.

Examples of the preferred embodiments of the glycosyl hesperetin of the present invention include those with an α-glycosyl hesperidin content of at least 50% but less than 100%, when the glycosyl hesperetin is α-glycosyl hesperidin such as α-glucosyl hesperidin.

In the case of providing the glycosyl hesperetin of the present invention as a source of α-glucosyl hesperidin at a lesser cost, the upper limit of the α-glucosyl hesperidin content in the glycosyl hesperetin of the present invention can be usually 90% or lower to easily provide it on an industrially, in a relatively larger amount and at a lesser cost; preferably 85% or lower for providing it at a more lesser cost; and more preferably 80% or lower for providing it at a furthermore lesser cost. While, the lower limit of the α-glucosyl hesperidin content is usually at least 60%, 65%, or 70% for a similar reason as in the above-mentioned glycosyl hesperetin content. In particular, examples of the preferred embodiments of the glycosyl hesperetin of the present invention include those with an α-glucosyl hesperidin content of 60 to 90%, d.s.b.

The aforesaid glycosyl hesperetin content in the glycosyl hesperetin of the present invention can be determined by any measuring apparatuses used commonly in the art. An example of such is as follows: The glycosyl hesperetin content is determined by sampling the glycosyl hesperetin of the present invention; diluting or dissolving the sample with refined water to give a concentration of, for example, 0.1 w/w %; filtering the resulting solution with a commercialized 0.45 μm membrane filter; subjecting the filtrate to high-performance liquid chromatography (called "HPLC", hereinafter) using a reagent grade hesperidin, commercialized by Wako Pure Chemical Industries, Ltd., Tokyo, Japan, as a standard substance under the following conditions; and calculating the glycosyl hesperetin content based on the area of each peak appeared in the chromatogram at an UV wavelength of 280 nm and the molecular weight corresponding to each peak for each glycosyl hesperetin such as hesperidin, α-glycosyl hesperidin (α-glucosyl hesperidin, etc.), or 7-O-β-glucosyl hesperetin. Quantification of glycosyl hesperetin is outlined below:

<HPLC Analytical Conditions>
- HPLC Apparatus: "LC-20AD", commercialized by SHIMADZU CORPORATION, Kyoto, Japan
- Degasser: "DGU-20A3", commercialized by SHIMADZU CORPORATION, Kyoto, Japan
- Column: "CAPCELL PAK C18 UG 120", commercialized by Shiseido Co., Ltd., Tokyo, Japan
- Sample injection volume: 10 μL
- Eluant: water/acetonitrile/acetic acid (80/20/0.01 (by volume ratio))
- Flow rate: 0.7 mL/min
- Temperature: 40° C.
- Detection: "SPD-20A", a UV detector, commercialized by SHIMADZU CORPORATION, Kyoto, Japan
- Measurement wavelength: 280 nm
- Data processor: "CHROMATOPAC C-R7A" commercialized by SHIMADZU CORPORATION, Kyoto, Japan <Quantification of Glycosyl Hesperetin>

(1) Content of hesperidin: it is analyzed on HPLC and calculated based on the ratio of a peak area of hesperidin in a sample to that of a reagent grade hesperidin as a standard substance, commercialized by Wako Pure Chemical Industries, Tokyo, Japan, at a prescribed concentration.

(2) Content of α-glucosyl hesperidin: It is analyzed on HPLC and calculated based on the ratio of a peak area of α-glucosyl hesperidin in a sample to that of a reagent grade hesperidin as a standard substance, commercialized by Wako Pure Chemical Industries, Tokyo, Japan, at a prescribed concentration; and on the molecular weight ratio of α-glucosyl hesperetin to hesperidin.

(3) Content of 7-O-β-glucosyl hesperetin: It is analyzed on HPLC and calculated based on the ratio of the peak area of 7-O-β-glucosyl hesperetin in a sample to that of a reagent grade hesperidin as a standard substance, commercialized by Wako Pure Chemical Industries, Tokyo, Japan, at a prescribed concentration; and on the molecular weight ratio of α-glucosyl hesperetin to hesperidin.

(4) Contents of other glycosyl hesperetins: They are analyzed on HPLC and calculated based on the ratio of a peak area of each of the other glycosyl hesperetins in a sample to that of a reagent grade hesperidin as a standard substance, commercialized by Wako Pure Chemical Industries, Tokyo, Japan, at a prescribed concentration; and on the ratio of the molecular weight of respective other α-glucosyl hesperetins to hesperidin.

The term "the content of glycosyl hesperetin, d.s.b." in the glycosyl hesperetin of the present invention means a percentage (%) of the total content of glycosyl hesperetins determined in the above (1) to (4) to the weight, d.s.b., of the glycosyl hesperetin of the present invention used as a sample.

Compared to conventional products, the glycosyl hesperetin of the present invention is the one that is significantly reduced in miscellaneous tastes and that, having been obtained with referencing the furfural content, does not substantially contain furfural. In other words, the furfural content in the glycosyl hesperetin of the present invention is an index for obtaining glycosyl hesperetin that is significantly reduced in miscellaneous tastes, and the specification discloses a method for producing such glycosyl hesperetin using the furfural content as the index. Needless to say, the lower the furfural content the more the miscellaneous tastes of glycosyl hesperetin is reduced significantly.

During the processes of variously examining the glycosyl hesperetin of the present invention, the present inventors found that, among the glycosyl hesperetins of the present invention, those which do not substantially contain furfural and 4-vinyl anisole (abbreviated as "4-VA", hereinafter) also known as 4-methoxystylene, a kind of phenol ether, are more distinctly reduced in miscellaneous tastes, as well as coloration, among the glycosyl hesperetins of the present invention. The content of 4-VA, which is estimated to be a possible ingredient generated from any one of the materials used for producing the glycosyl hesperetin of the present invention, is usually less than 30 ppb to the mass of the glycosyl hesperetin, d.s.b.; and the content of 4-VA is usually in a parallel relationship with the furfural content in glycosyl hesperetin that has a furfural content of less than 200 ppb. The term "substantially does not contain 4-VA" as referred to as in the present invention means that, similarly as in furfural, the content of 4-VA is in a significantly low level compared to conventional products. Concretely, the content of 4-VA in the glycosyl hesperetin of the present invention is usually less than 30 ppb, preferably less than 15 ppb, more preferably 10 ppb, furthermore preferably less than 5 ppb, more preferably less than 3 ppb, and furthermore preferably less than 2 ppb to the mass of the glycosyl hesperetin, d.s.b., when determined on the analytical method using the GC/MS analyzer shown in "(2) 4-VA" in the later described Experiment 1.

Further, the glycosyl hesperetin of the present invention has an advantageous feature of being significantly reduced in miscellaneous tastes as a defect of conventional products; or it has not only an advantageous feature of being significantly reduced in miscellaneous tastes compared to conventional products but retains such an advantageous feature even when heated after dissolved in an aqueous solution. The miscellaneous tastes of the glycosyl hesperetin of the present invention can be evaluated with the sensory evaluation by panelists shown in the later described "Experiment 2: Sensory test".

The glycosyl hesperetin of the present invention has an advantageous feature of being distinctly reduced in coloration compared to conventional products (may be called "coloration degree", hereinafter). The coloration degree of the glycosyl hesperetin of the present invention is determined with the method shown in "(2) Color tone and coloration degree" in the later described Experiment 1 and outlined as follows: An aqueous solution with a prescribed concentration of the glycosyl hesperetin of the present invention is subjected to a heat treatment in a sealed container, and the resulting solution is macroscopically observed for its color tone and measured for its absorbances of $OD_{420nm}$ and $OD_{720nm}$; at respective wavelengths of 420 nm and 720 nm, followed by calculating the difference between the above absorbances, $OD_{420nm}$ minus $OD_{720nm}$, to obtain a value for use as a coloration degree. Preferred embodiments of the glycosyl hesperetin of the present invention include those which have the above difference being less than 0.24, preferably 0.20 or lower, more preferably 0.17 or lower, and furthermore preferably 0 or higher but 0.15 or lower. Since conventional products have a defect of being distinctly increased in their coloration degree when heated, the above aqueous solution is intentionally heated in practicing this assay to accurately evaluate the coloration of the glycosyl hesperetin of the present invention per see and the degree of coloration by heating.

Preferred embodiments of the glycosyl hesperetin of the present invention include those which have an electric conductivity of less than 10 µS/cm, preferably less than 8 µS/cm, more preferably less than 6 µS/cm, furthermore preferably over 0 µS/cm but less than 4.5 µS/cm, when determined by preparing them into 1 w/w % aqueous solutions, heating the aqueous solutions at 100° C. for 30 min in respective sealed containers, and cooling the heated solutions to 20° C. before determining their electric conductivity. The electric conductivity can be determined with a conventional conductance meter. Since conventional products have an electric conductivity of over 10 µS/cm, the glycosyl hesperetin of the present invention has a characteristic feature of a lesser content of ionizable compounds compared to conventional products. The reason why the aqueous solutions of the glycosyl hesperetin of the present invention are heated in the above assay has been established in view of the dynamics of the aforesaid coloration degree.

Preferred embodiments of the glycosyl hesperetin of the present invention include those which have a relatively low content of calcium, potassium, magnesium, and sodium, which are ionic compounds that influence on the electric conductivity of the glycosyl hesperetin, compared to conventional products. The contents of calcium, potassium, magnesium, and sodium in the glycosyl hesperetin of the present invention are determined with a high-frequency inductively coupled plasma emission spectrometric analysis method, commonly used in the art. Examples of the glycosyl hesperetin of the present invention include those which have calcium, potassium, magnesium, and sodium contents of 1 ppm or lower, 0.1 ppm or lower, 0.2 ppm or lower, and 0.4 ppm or lower, respectively, against the glycosyl hesperetin, d.s.b.; more preferably 0.6 ppm or lower, 0.06 ppm or lower, 0.1 ppm or lower, and 0.3 ppm or lower, respectively; and more preferably 0 ppm or more but 0.5 ppm or lower, 0 ppm or more but 0.05 ppm or lower, 0 ppm or more but 0.08 ppm or lower, and 0 ppm or more but 0.2 ppm or lower, respectively.

Thus, it is judged that the glycosyl hesperetin of the present invention is reduced in the content of physiologically acceptable ionic compounds such as salts and other ionic components because, compared to conventional products, the glycosyl hesperetin is reduced in both electric conductivity and the concentration of metallic elements (or metallic ions) such as calcium, potassium, magnesium, and sodium.

The following are sequential explanations of the method for producing the glycosyl hesperetin and the method for reducing the miscellaneous tastes of glycosyl hesperetin-containing products according to the present invention.

The production method of the present invention is to produce glycosyl hesperetin, and it contains the steps of: (a) Preparing an aqueous solution containing hesperidin and a partial starch hydrolyzate; (b) allowing a saccharide-transferring enzyme to act on the resulting aqueous solution to form glycosyl hesperetin containing α-glucosyl hesperidin; and (c) collecting the formed glycosyl hesperetin; wherein one or more of the steps (a) to (c) are effected in the presence of a reducing agent or a reducing agent is added to a starting material(s) before practicing one or more of the steps (a) to (c) and/or added to the resulting product(s) of any one of the above steps. The following are sequential explanations of the production materials, enzymatic reactions such as saccharide-transferring/transglycosylation reactions, treatments with reducing agents, and purification methods used in the above production method.

Production Materials:

Examples of the hesperidin as a production material used in the present disclosure include any of the hesperidins used in producing conventional products and those with a relatively high purity of hesperidin, as well as others, having a relatively low purity of hesperidin, such as extracts, juices, and partially-purified products deriving from hesperidin-containing plants, one or more of which can be appropriately used in combination. Examples of the aforesaid hesperidin-containing plants include, for example, citruses belonging to the genus Citrus of the family Rutaceae such as mandarins, oranges, flavorful acid citruses, mixed breed citruses, tangors, tangelos, shaddocks, kumquats, and bitter oranges; wherein representative hesperidin-containing parts are fruits, peels, seeds, unripe fruits, etc.

Examples of the partial starch hydrolyzate as a production material used in the present disclosure include those which enable transglycosylation onto hesperidin to form α-glycosyl hesperidin as glycosyl hesperetin, when the later described glycosyltransferase is allowed to act on them; partial starch hydrolyzates such as amyloses, dextrins, cyclodextrins, maltooligosaccharides, as well as liquefied and gelatinized starches, one or more of which can be arbitrarily selected.

The amount of a partial starch hydrolyzate used in the later described enzymatic reaction is usually about 0.1 to about 150 folds, preferably about 1 to about 100 folds, and more preferably about 2 to about 50 folds of the amount of the material hesperidin by mass. In the enzymatic reaction, saccharides deriving from partial starch hydrolyzates are glycosyltransferred onto hesperidin to efficiently form α-glycosyl hesperidin, wherein partial starch hydrolyzates should preferably be used in an excessive amount to the hesperidin so as not to remain hesperidin intact in an enzymatic reaction system as low as possible. The reason is that, in the later described purification step, partial starch hydrolyzates and saccharides derived therefrom can be relatively easily separable from α-glycosyl hesperidin; however, since hesperidin shows the same dynamics as α-glycosyl hesperidin and it is hardly separable from α-glycosyl hesperidin, the water solubility of the resulting glycosyl hesperetin will inconveniently decrease as a whole, when intact hesperidin with a distinctly-low water solubility is still remained in a considerably large amount.

Enzymatic Reaction:

The term "enzymatic reaction" as referred to as in the present invention means an enzymatic reaction of allowing glycosyltransferase to act on hesperidin and a partial starch hydrolyzate as the aforesaid production materials to form α-glycosyl hesperidin.

Examples of the glycosyltransferase used in the enzymatic reaction include α-glucosidase (EC 3.2.1.20), cyclomaltodextrin glucanotransferase (EC 2.4.1.19, called "CGTase", hereinafter), and α-amylase (EC 3.2.1.1), etc. Examples of the above α-glucosidase include those which are derived from animal and plant tissues such as pig liver and buckwheat seed; and those which are derived from cultures of fungi belonging to the genera *Mucor, Penicillium*, and *Aspergillus* including *Aspergillus niger*, etc., or other cultures obtained through culturing of yeasts of the genus *Saccharomyces* in nutrient culture media. Examples of the CGTase include those which are derived from the genera *Bacillus, Geobacillus, Klebsiella, Paenibacillus, Thermococcus, Thermoanaerobacter, Brevibacterium, Pyrococcus, Brevibacillus*, and *Saccharomyces*. Examples of the α-amylase include those which are derived from cultures of bacteria of the genus *Geobacillus* or fungi of the genus *Aspergillus* including *Aspergillus niger*, one or more of which can be used in an appropriate combination. Any one of natural or recombinant glycosyltransferases can be used as the above glycosyltransferases as long as they attain the objects of the present invention, and if commercialized products thereof are available, they can be also appropriately used. All the above glycosyltransferases should not necessarily be used after purification, and usually they can be used even in a crude enzyme form as long as attaining the objects of the present invention.

Upon the use of the above natural or recombinant glycosyltransferases, the production yield of α-glycosyl hesperidin can be increased by selecting a partial starch hydrolyzate suitable for the above enzymes.

In the case of using the above α-glucosidase, maltooligosaccharides such as maltose, maltotriose, and maltotetraose or partial starch hydrolyzates with a dextrose equivalent (DE) of about 10 to about 70 can be suitably used; in the case of using the above CGTase is used, α-, β- or γ-cyclodextrin or those which are ranging from liquefied starch with a DE of one or lower to partial starch hydrolyzates with a DE of about 60 can be suitably used; and in the case of using the above α-amylase, partial starch hydrolyzates that are ranging from liquefied starches with a DE of one or lower to dextrins with a DE of about 30 can be suitably used.

Examples of the hesperidin-containing solutions used in the enzymatic reactions include those which contain hesperidin as much as possible; preferably used are suspensions of hesperidin or solutions containing hesperidin at relatively high concentrations, prepared by dissolving hesperidin in media such as water at relatively high temperatures or under alkaline pHs of over 7.0 using alkaline agents. As such alkaline agents, the following are appropriately used; one or more of about 0.1 to about 1.0 N strongly alkaline aqueous solutions of sodium hydroxide, potassium hydroxide, sodium carbonate, calcium hydroxide, and aqueous ammonia.

The concentration of hesperidin in a solution form, prepared with hesperidin and an alkaline agent, is usually about 0.005 w/v % or higher, preferably about 0.05 to 10 w/v %, more preferably about 0.5 to about 10 w/v %, and furthermore preferably about 1 to about 10 w/v %.

When used in a suspension form prepared without using any alkaline agent, hesperidin is suspended in a medium such as water into a suspension form, wherein the concentration of hesperidin is usually about 0.1 to about 2 w/v %, preferably about 0.2 to about 2 w/v %, and more preferably about 0.3 to about 2 w/v %.

Although the temperature and time, at which glycosyltransferase is allowed to act on hesperidin and a partial starch hydrolyzate, vary depending on the concentrations of hesperidin and a partial starch hydrolyzate used in such an enzymatic reaction, as well as on the type, optimum temperature, optimum pH, or the amount of the enzyme used, the temperature is usually about 50 to about 100° C., preferably about 60 to about 90° C., more preferably about 70 to about 90° C.; and the time is about 5 to about 100 hours, preferably about 10 to about 80 hours, and more preferably about 20 to about 70 hours.

Although the pH and temperature, at which glycosyltransferase is allowed to act on an alkaline solution with a relatively high concentration of hesperidin, vary depending on the type, optimum pH, optimum temperature, or the amount of the enzyme used, as well as on the concentration of hesperidin, they should be adjusted to a highest possible pH and temperature at which the enzyme is functionable; wherein the pH is about 7.5 to about 10, and preferably about 8 to about 10; and the temperature is about 40 to about 80° C., and preferably about 50 to about 80° C. Since hesperidin in itself is susceptible to decompose in alkaline solutions, it should preferably be kept under light-shielded and anaerobic conditions as much as possible to avoid such decomposition.

When glycosyltransferase is allowed to act on hesperidin in a suspension form, the pH of the enzyme employed varies depending on the type, optimum temperature, optimum pH, or the amount of the enzyme used, as well as the concentration of hesperidin in the suspension; however, it is usually a pH ranging from about 4 to about 7, preferably about 4.5 to about 6.5.

Further, if necessary, the glycosyltransferring or saccharide-transferring reaction of hesperidin can be arbitrarily facilitated by increasing the solubility of hesperidin before the prescribed enzymatic reaction in such a manner of allowing an appropriate amount of one or more high water-compatible organic solvents such as lower alcohols or ketones including methanol, ethanol, n-propanol, isopropanol, n-butanol, acetol, and acetone to coexist in high hesperidin content solutions, particularly high hesperidin content aqueous solutions.

In terms of economic aspects, the amount and the reaction time of enzymes are closely related each other, and therefore the amount of glycosyltransferase is usually, appropriately set to a level sufficient for terminating the enzymatic reaction within about 5 to about 150 hours, preferably about 10 to about 100 hours, more preferably about 20 to about 80 hours, depending on the type of the enzyme used. By using an immobilized glycosyltransferase, a desired enzymatic reaction can be appropriately proceeded repeatedly in a batch-wise or consecutive manner.

Depending on use, the enzymatic reaction solution containing hesperidin and α-glycosyl hesperidin, obtained after the above glycosyltransferring reaction, can be used intact or successively subjected to purification using porous synthetic adsorbing resins and to partial hydrolysis with amylase such as glucoamylase (EC 3.2.1.3) or β-amylase (EC 3.2.1.2) to lower the number of α-D-glucosyl residues of α-glycosyl hesperidin. For example, in the case of using the above glucoamylase in the enzymatic reaction, α-maltosyl hesperidin or higher molecules can be hydrolyzed to form and accumulate α-glucosyl hesperidin along with glucose. While, in the case of using the above β-amylase, α-maltotriosyl hesperidin and higher molecules can be hydrolyzed to form and accumulate a mixture of α-glucosyl hesperidin and α-maltosyl hesperidin along with maltose.

Glycosyl hesperetin with a relatively-high water solubility is prepared by allowing glucoamylase and α-L-rhamnosidase simultaneously at once or successively in a random order to act on an enzymatic reaction solution containing hesperidin and α-glycosyl hesperidin obtained after the glycosyltransferring reaction, whereby equimolar or more glucoses linked via α-linkage in the rutinose structure of α-glycosyl hesperidin are released to transform r-glycosyl hesperidin into α-glucosyl hesperidin, resulting in an increment of the content of α-glucosyl hesperidin and a conversion of hesperidin with a relatively-low water solubility into 7-O-β-monoglucosyl hesperetin with a relatively-high water solubility.

Similar to glycosyltransferase, glucoamylase and α-L-rhamnosidase have a close relationship between their enzyme amounts and enzymatic reaction times, and therefore, in view of economic aspects, the amount of the above enzymes is preferably set to a level sufficient for terminating their enzymatic reactions within about 5 to about 150 hours, preferably about 10 to about 100 hours, more preferably about 20 to about 80 hours, depending on the types of the enzymes used. By using an immobilized α-L-rhamnosidase, a desired enzymatic reaction can be appropriately conducted repeatedly or continuously in a batch-wise or consecutive manner.

Treatment with Reducing Agent:

The term "treatment with reducing agent" as referred to as in the present disclosure means a treatment of significantly reducing the miscellaneous tastes of glycosyl hesperetin with a reducing agent; or a prescribed amount of the later described reducing agent(s) is/are either used in one or more of the following steps of (a) preparing an aqueous solution containing hesperidin and partial starch hydrolyzate, (b) allowing glycosyltransferase to act on the resulting aqueous solution to form glycosyl hesperetin containing α-glucosyl hesperidin, and (c) collecting the formed glycosyl hesperetin; or added to any one or more of the starting materials prior to the above steps (a) to (c) and/or of the resulting products in these steps.

The reducing agents usable in the present invention should not specifically be restricted as long as they attain the desired objects of the present invention, and there can be used any conventional organic or inorganic reducing agents available in the art. Since the glycosyl hesperetin of the present invention is, however, presupposed to be used primarily for humans, desirably used are those which are high in safety and superior in stability and handleability.

Concrete examples of the reducing agents preferably used in the present invention include inorganic reducing agents such as hydroxylamines, hydrazine compounds, chlorine dioxide, hydrogen, hydrogen compounds (hydrogen sulfide, sodium borohydride, lithium aluminum hydride, potassium aluminum hydride, etc.), sulfur compounds (sulfur dioxide, thiourea dioxide, thiosulfate, sulfite, ferrous sulfate, sodium persulfate, potassium persulfate, ammonium persulfate, calcium sulfite, etc.), nitrite, tin chloride, ferrous chloride, potassium iodide, hydrogen peroxide, diluted benzoyl peroxide, hydroperoxide, and chlorite such as sodium chlorite; and organic reducing agents such as phenols, amines, quinones, polyamines, formic acid and salts thereof, oxalic acid and salts thereof, citric acid and salts thereof, thiourea dioxide, reducing saccharides, benzoyl peroxide, benzoyl persulfate, diisobutylaluminum hydride, catechin, quercetin, tocopherol, gallic acid and esters thereof, ethylenediaminetetraacetate (EDTA), dithiothreitol, reduced glutathione, and polyphenols. One or more of the above organic and inorganic reducing agents can be used in appropriate combinations.

Among the above inorganic and organic reducing agents, the former is more preferably used because it significantly lowers the miscellaneous tastes inherent to conventional products and provides a high-quality glycosyl hesperetin with decreased odor. Though the reason is not sure, it is estimable as follows: It presumes that organic reducing agents are organic compounds and thus they may generate miscellaneous tastes or coloration and they themselves or their decompositions still remain in the processes of producing the glycosyl hesperetin of the present invention without being completely removed, giving a negative influence on the quality of glycosyl hesperetin.

Among the inorganic reducing agents, what they call subsulfates (may be called sulfites), which are composed of a metal ion and $SO_2^-$, $HSO_3^-$, $SO_3^{2-}$, $S_2O_4^{2-}$, or $S_2O_7^{2-}$ ion are superior in safety, stability, and handleability, are more suitably used as reducing agents in practicing the present invention. In particular, the following inorganic reducing agents can be most suitably used in the present disclosure: Subsulfates such as sodium sulfite, potassium sulfite, sodium hydrogen sulfite, sodium hyposulfite, potassium hyposulfite, sodium pyrosulfite, potassium pyrosulfite, sodium metasulfite, potassium metasulfite, sodium metabisulfite, and potassium metabisulfite.

The above-mentioned reducing agents are used in any one of the steps of producing the glycosyl hesperetin or used in the starting material and/or the resulting product of the step; however, the instant objects of the present invention can be attained with a more lesser amount of the reducing agent(s) when the agent(s) is/are used in portions in two or more of the steps or added to the starting material(s) before practicing one or more of the steps and/or added to the resulting product(s) in any of the steps.

The total additive amount of the above reducing agent(s) used in each of the above steps (a) to (c) is usually at least 0.001%, preferably 0.01 to 3%, more preferably 0.01 to 1%, and furthermore preferably 0.01 to 0.5% to the mass of the enzymatic reaction solution, obtained after the above step (b), or to the one obtained after completion of all the enzymatic reactions, when any enzyme(s) other than the glycosyltransferase is used. In the case of being used the reducing agent(s) before the step (c), the remaining agent(s) is/are usually, substantially removed in the purification step; accordingly, no reducing agent is substantially detected in the resulting glycosyl hesperetin obtained as a final product. The total amount of the reducing agents, added at a time or several times during the above steps, is usually at least 0.001%, preferably at least 0.01%, and more preferably 0.01 to 1% by mass to the mass of the enzymatic reaction solution 0 obtained after the above enzymatic reaction. Referring to the temperatures at which the reducing agents are added, they usually mean the temperatures employed in the above steps (a) to (c), or optionally include other temperatures exceeding the above temperatures. Concrete examples of such are temperatures not lower than ambient temperature, preferably at least 50° C., more preferably at least 70° C., more preferably at least 80° C., and furthermore preferably 90 to 120° C.

Purification Method:

The enzymatic reaction solutions thus obtained can be used intact as the glycosyl hesperetin of the present invention; however, they are usually prepared into glycosyl hesperetins in the form of a liquid, solid, or powder by appropriately employing, either alone or in combination with, one or more means of separation methods, filtration methods, purification methods using porous synthetic resins, concentration methods, spraying methods, drying methods, etc., all of which are conventionally known in the art.

Examples of the above porous synthetic resins include synthetic resins such as non-ionic styrene-divinyl benzene copolymers, phenol-formalin resins, acrylate resins, and methacrylate resins, all of which have no ionicity but have a porous and large adsorption-surface area: Resins with trade names of AMBERLITE XAD-1, AMBERLITE XAD-2, AMBERLITE XAD-4, AMBERLITE XAD-7, AMBERLITE XAD-8, AMBERLITE XAD-11, AMBERLITE XAD-12, etc., commercialized by Rohm & Hass Company, Philadelphia, USA; resins with trade names of DIAION HP-10, DIAION HP-20, DIAION HP-30, DIAION HP-40, DIAION HP-50, DIAION HP-2MG, SEPABEADS SP70, SEPABEADS SP207, SEPABEADS SP700, SEPABEADS SP800, etc., commercialized by Mitsubishi Chemical Industries Ltd., Tokyo, Japan; and other resins with trade manes of IMACTI Syn-42, IMACTI Syn-44, IMACTI Syn-46, etc., commercialized by IMACTI Company, Amsterdam, the Kingdom of the Netherlands.

According to the purification methods using porous synthetic resins, glycosyl hesperetin adsorbs onto the porous synthetic resins, while the remaining partial starch hydrolyzates, water-soluble saccharides, etc., are eluted from columns packed with the resins without adsorption onto the resins, when enzymatic reaction solutions are fed to the columns. In this case, hesperidin, 7-O-β-glucosyl hesperetin, and α-glycosyl hesperetin as glycosyl hesperetins usually behave similarly, and therefore, they could not be separated one another by using porous synthetic resins; however, although the handlings become complicated and the yields decrease, glycosyl hesperetins, which selectively adsorb onto columns packed with porous synthetic resins, are washed out with solvents such as diluted alkalis or water, and then fed with relatively small amounts of organic solvents or mixture solutions of organic solvents and water, i.e., aqueous methanol or ethanol solutions, to firstly elute α-glycosyl hesperidin from the columns and then intact hesperidin is eluted by increasing either the feeding volumes or the concentrations of organic solvents. The resulting solutions containing glycosyl hesperetins are treated with evaporation, followed by removing the remaining organic solvents and concentrating the resulting solutions up to prescribed concentrations to obtain the glycosyl hesperetins of the present invention with reduced hesperidin contents. Since the above step of eluting glycosyl hesperetin with the above-mentioned organic solvents would also act as a step of regenerating the porous synthetic resins, enabling a repetition use of the resins as a merit.

The glycosyl hesperetin with an increased content of glycosyl hesperetin in a liquid form according to the present invention can be produced in such a manner of, after completion of the enzymatic reactions and before contacting the resulting enzymatic reaction solutions with the porous synthetic resins, for example, removing insolubles generated when the enzymatic reaction solutions are heated, removing proteinous substances in the reaction solutions by treating them with magnesium aluminosilicate, magnesium aluminate, etc.; or desalting the solutions with strong-acid ion-exchange resins (H-form), intermediately-basic/weakly-basic ion-exchange resins (OH-form), or the like.

Further, the above-mentioned liquid glycosyl hesperetin can be arbitrarily dried and pulverized into a particulate composition of glycosyl hesperetin by conventional drying methods.

In this way, there can be produced glycosyl hesperetin in which the miscellaneous tastes, characteristic of conventional products as a defect, are effectively, significantly reduced. While, the present inventors confirmed that the miscellaneous tastes of conventional products without any treatment of reducing agents are not substantially changed with mere use of the above-mentioned purification methods: Conventional purification methods, which use, for example, the above-mentioned porous synthetic resins commonly used in producing conventional products, advantageously, simultaneously removes concomitants such as water-soluble salts, as well as partial starch hydrolyzates and water-soluble saccharides; however, it is hard to significantly reduce the miscellaneous tastes characteristic of conventional products, regardless how to use the above purification methods. It is estimable that any causative substance of the miscellaneous tastes, contained in glycosyl hesperetins, exhibits similar dynamics of adsorption onto and desorption from porous synthetic resins to those of glycosyl hesperetin, and therefore such causative substance could not be separable from glycosyl hesperetin.

Compared to conventional products, the glycosyl hesperetin of the present invention is significantly reduced in miscellaneous tastes as well as in both electric conductivity and the content of ionic compounds relating to the electric conductivity. Examples of such ionic compounds include compounds such as narirutin, diosmin, and neoponcirin, which are intrinsically coexisted in hesperidin as a material for the glycosyl hesperetin; glucosyl narirutin, glucosyl neoponcirin, etc., as enzymatic reaction byproducts, as well as decompositions thereof and compounds closely relating to such decompositions; furfurals such as furfural used as an index for practicing the present invention, furfuryl alcohol, and hydroxymethyl furfural, as well as salts thereof; and other compounds that release metallic cations of calcium, potassium, magnesium, sodium, etc., when in solution forms; all of which are derived from the production materials for the glycosyl hesperetin or formed as side products during its production steps. Usually, the glycosyl hesperetin of the present invention only slightly contains the above ingredients such as the above-identified narirutin, diosmin, neoponcirin, glucosyl narirutin, and glucosyl neoponcirin.

As described above, the glycosyl hesperetin, which is significantly reduced in furfural content, according to the present invention is a high-quality glycosyl hesperetin whose miscellaneous tastes are significantly reduced compared to conventional products.

The mechanism of how glycosyl hesperetin, whose miscellaneous tastes are significantly reduced, is attained by the method for producing glycosyl hesperetin of the present invention is uncertain, however, it can be estimated as follows:
(1) In producing the glycosyl hesperetin of the present invention, the prescribed reducing agents act on substances, as causatives for miscellaneous tastes deriving from the production materials, to mask, decompose, or modify them to obtain a desired glycosyl hesperetin that is significantly reduced in miscellaneous tastes;
(2) In the step(s) of producing the glycosyl hesperetin of the present invention, the prescribed reducing agents reduce or inhibit the formation of substances as causatives for miscellaneous tastes; or mask, decompose, or modify the formed substances to obtain a desired glycosyl hesperetin that is significantly reduced in miscellaneous tastes; or
(3) The substances as shown in the above items (1) and (2) are modified with the prescribed reducing agents to facilitate the separation of glycosyl hesperetin in a purification step using porous synthetic adsorbents, etc., and to obtain a desired glycosyl hesperetin that is significantly reduced in miscellaneous tastes.

The method for decreasing the miscellaneous tastes of a composition containing glycosyl hesperetin according to the present invention is the one that contains a step of allowing such a composition to contact with a prescribed reducing agent. The term "a composition containing glycosyl hesperetin", as referred to as in the method according to the present invention means any one of those in general which contain glycosyl hesperetin as a main ingredient. According to the method, the coloration of a composition containing glycosyl hesperetin can be also effectively, distinctly decreased. The conditions for contacting compositions containing glycosyl hesperetin with a prescribed reducing agent should preferably be performed, rather than in a solid state, in a solution or suspension state using an appropriate solvent such as water. Examples of the glycosyl hesperetin to be contacted with a reducing agent include glycosyl hesperetins containing one or more of hesperidin, α-glycosyl hesperidin, and 7-O-β-glucosyl hesperetin. Examples of such compositions containing glycosyl hesperetin include those which contain glycosyl hesperetin in an amount of, usually, at least 70% but less than 100%, preferably at least 80% but less than 100%, and more preferably at least 90% but less than 100%.

The reducing agents used in the method for decreasing the miscellaneous tastes of the glycosyl hesperetin of the present invention are similar to those which are used in the method for producing the glycosyl hesperetin of the present invention. The amount of respective reducing agents to be added to glycosyl hesperetin is usually at least 0.00001%, preferably 0.0001 to 0.5%, more preferably 0.001 to 0.4%, and furthermore preferably 0.001 to 0.3% by mass to the mass of the glycosyl hesperetin, d.s.b., where the resulting mixture is mixed to homogeneity for allowing glycosyl hesperetin to contact with the reducing agents, resulting in significantly reducing the characteristic miscellaneous tastes of conventional products.

The glycosyl hesperetin of the present invention thus obtained can be provided, for example, in various forms of liquids, pastes, solids, granules, or powders.

Since the glycosyl hesperetin, obtained by the method for producing glycosyl hesperetin and the method for decreasing the miscellaneous tastes of a composition containing glycosyl hesperetin according to the present invention, is in itself significantly reduced in its miscellaneous tastes and also distinctly reduced in its coloration and odor, as well as being improved in its thermostability; it exerts advantageous features of being significantly reduced in its miscellaneous tastes and distinctly reduced in its coloration and odor compared to those with conventional products, even when heated at 80 to 100° C. for at least 30 min or stored at an ambient temperature or at a temperature slightly higher than the ambient temperature for several tens of minutes to several months during a step of its incorporation or after its incorporation into food products, preferences including tobaccos and cigarettes, cosmetics, pharmaceuticals such as agents for susceptive diseases, quasi-drugs, chemicals, industrial feedstock and materials, feeds, baits, clothes, sundries including commodities, or plastic products. Accordingly, since the glycosyl hesperetin of the present invention well harmonizes with substances having tastes such as acidity, saltiness, astringency, delicious taste, or bitterness, and has a relatively-high acid tolerance and thermostability, it can be widely, advantageously used in food products in general including dietary supplements such as foods for specified health uses: Seasonings; Japanese-style confectionaries; Western-style confectionaries; frozen sweets; beverages including teas such as green teas, black teas, herb teas, juices, soft drinks, coffees, cocoas, and tonic drinks; alcohols such as Japanese sakes, whiskies, wines, liqueurs, and spirits; spreads; pastes; pickles; bottled and canned food products; processed meats; fish meats/fishery products; processed milk/egg products; processed vegetable products; processed fruit products; and processed cereal products, etc. Also, the glycosyl hesperetin of the present invention can be advantageously used in feeds and baits for breeding animals such as domestic animals, poultries, bees, silkworms, and fishes as a vitamin P-enriched agent, preference-improving agent, etc.

Further, the glycosyl hesperetin of the present invention can be used as a food for beauty and appropriately incorporated into foods for beauty and other foods including beverages.

The glycosyl hesperetin of the present invention can be used in the following items: Cleaning/cleansing cosmetics such as soaps, cosmetic soaps, Chinese medicine soaps, skin washing powders, cleansing creams, cleansing foams, facial rinses, body shampoos, body rinses, shampoos, rinses, and hair-washing powders; hair care cosmetic products such as waveset lotions, hair blows, tiques, hair creams, pomades, hair sprays, hair liquids, hair tonics, hair lotions, hair restorers, hair dyes, and scalp greases; basic skin-care cosmetic products such as cosmetic lotions, vanishing creams, emollient creams, emollient lotions, pack cosmetics (including peel off-type jelly-like cosmetics, jelly-like-swab-type cosmetics, paste-like-rinse-type cosmetics, and powder cosmetics), cleansing creams, cold creams, hand creams, hand lotions, milky lotions, moisturizing lotions, after shave lotions, shave lotions, pre-shave creams, after shave creams, after shave foams, pre-shave creams, cosmetic oils, and baby oils; make-up preparations such as foundations in the form of a liquid, cream, solid, or the like, talcum powders, baby powders, body powders, perfume powders, makeup bases, face powders in the form of a cream, paste, liquid, solid, powder, or the like, eye shadows, eye creams, mascaras, pencils, eyelash cosmetics, blushers, or cheek moisturizers; aromatic cosmetics such as perfumes, solid perfumes, powdered perfumes, eau de colognes, perfume colognes, or eau de toilettes; suntan or sunscreen cosmetics such as suntan creams, suntan lotions, suntan oils, sunscreen creams, sunscreen lotions, or sunscreen oils; nail cosmetics such as manicures, pedicures, nail colors, nail lacquers, enamel removers, nail creams, or nail cosmetics; eyeliner cosmetics; lipstick/rouge cosmetics such as lipsticks, lip balms, muddy colored lipsticks or rouges, or lip glosses; oral cosmetics such as oral odor preventives, toothpastes/dentifrices, or mouthwashes; bath cosmetics such as bath salts, bath oils, or bathing cosmetics; skin-beautifying agents; skin-whitening agents; and anti-aging inhibitors and preventives. Also, the glycosyl hesperetin of the present invention can be preferably used in plastic products as an ultraviolet-absorbing agent or deterioration-inhibitory agent. Further, the glycosyl hesperetin of the present invention can be arbitrarily incorporated into preferences and agents for susceptive diseases such as prophylactic and therapeutic agents for susceptive diseases in the form of, for example, a solid, paste, or liquid, such as tobaccos, troches, liver-oil drops, vitamin complexes, mouth refrigerants, cachous, gargles, intubational nutritions, internal medicines, or injections. In addition, the glycosyl hesperetin of the present invention can be also preferably used in chemicals, industrial feedstock and materials, feeds, baits, clothes, sundries including commodities, or plastic products.

The glycosyl hesperetin of the present invention is used in an amount of, usually, at least about 0.0001%, preferably, about 0.001 to about 50%, more preferably about 0.01 to about 30%, furthermore preferably about 0.01 to about 20%, and more preferably about 0.01 to about 10% to the total mass of any one of the above-mentioned compositions or articles.

The term "susceptive diseases" as referred to as in the specification means diseases in general which can be prevented or treated with glycosyl hesperetin; examples of such include glycosyl hesperetin susceptive diseases, for example, viral diseases, bacterial diseases, traumatic diseases, immunopathies, rheumatisms, diabetics, allergic diseases, abnormality of lipid metabolism, circulatory diseases, and malignant tumors, which can be prevented or treated with glycosyl hesperetin. The form of the prophylactic/therapeutic agent for glycosyl hesperetin susceptive diseases can be appropriately chosen from among the following, depending on its purpose of use; liquids such as nebulas, ophthalmic solutions, collunariums, gargles, or injections; pastes such as ointments, cataplasms, or creams; and solids such as powders, powdered medicines, granules, tablets, or capsules. In preparing pharmaceuticals, other ingredients such as medicinal ingredients, physiologically active substances, antibiotics, adjuvants, fillers, excipients, stabilizers, colors, flavors, preservatives, antiseptics, or bacteriostats, one or more of which can be arbitrarily used in combination, if necessary.

The dose of the glycosyl hesperetin of the present invention can be appropriately controlled depending on the content, administration route, and administration frequency of the glycosyl hesperetin, as well as the symptoms of subjects to be administered therewith. The glycosyl hesperetin of the present invention is usually used in the range of about 0.001 to about 10 g/adult/day, preferably about 0.01 to about 5 g/adult/day, and more preferably about 0.05 to about 1 g/adult/day, d.s.b.

Examples of the method for incorporating the glycosyl hesperetin of the present invention into various compositions include one or more of conventional mixing, kneading, dissolving, soaking, penetrating, dispersing, applying, spraying, injecting, etc., one or more of which can be used alone or in an appropriate combination before completion of each of the compositions. The compositions are, for example, food products, preferences, cosmetics, pharmaceuticals such as agents for susceptive diseases, quasi-drugs, chemicals, industrial feedstock/materials, feeds, baits, clothes, sundries including commodities, or plastic products. The above compositions incorporated with the glycosyl hesperetin of the present invention exert actual benefits that the odors as well as miscellaneous tastes and colorations of the compositions are effectively, distinctly reduced even when stored at the temperatures as mentioned above for several tens of minutes to several months, compared to those incorporated with conventional products. Similar to conventional products, the glycosyl hesperetin of the present invention can be advantageously used in various compounds or compositions not only as a vitamin P-enriched agent but as a natural antioxidant, stabilizer, quality-improver, prophylactic agent, therapeutic agent, or ultraviolet-absorbing agent.

The following experiments explain the glycosyl hesperetin of the present invention in more detail:

Experiment 1: Property of Particulate Glycosyl Hesperetin

Except for using 0.1, 0.09, 0.07, or 0.04% of sodium pyrosulfite as a reducing agent in the later disclosed Example 1, four types of pulverized glycosyl hesperetins (test samples 5 to 8: the present invention) were prepared similar to the method of Example 1. While, as a control, except for not using any reducing agent in the methods of Examples 1, 3, 4, and 5, four types of pulverized glycosyl hesperetins (test samples 1 to 4: conventional products) were prepared similar to the above methods. Among the test samples 1 to 4, the test sample 1 is equivalent to the pulverized glycosyl hesperetin, obtained in the later disclosed Example for Reference 1.

(1) Furfural Content

Test samples 1 to 8 were respectively determined for their furfural contents by the following procedures and apparatuses:

<A. Preparation of Samples>

(a) A half gram, d.s.b., of any one of the above pulverized glycosyl hesperetins as test samples was placed in a 50-mL stoppered Erlenmeyer flask;

(b) Each of the pulverized glycosyl hesperetins is added with and dissolved in 5.0 mL of deionized water and added with 20 µL of 0.0025% cyclohexanol as a surrogate substance for use as an index for determining the recovery rate of each test sample upon analysis;

(c) One and half grams of sodium chloride is further added to and dissolved in each of the above resulting solutions, then each of the resulting mixtures is added with three milliliters of diethyl ether, a special grade reagent, commercialized by Wako Pure Chemical Industries, Ltd., Osaka, Japan, and stirred at 700 rpm for 10 min;

(d) Each of the resulting mixture is totally placed in a separatory funnel and allowed to stand for 10 min, followed by collecting the diethyl ether layer, dehydrating the layer with anhydrous sodium sulfate, and concentrating the dehydrated solution under a nitrogen-gas stream up to give a volume of about 200 µL;

(e) One microliter of the resulting concentrate is collected and subjected to a GC/MS analyzer; and (f) As a control, except for using a reagent grade furfural, a special grade specimen, commercialized by Tokyo Chemical Industry Co., Ltd., Tokyo, Japan, in place of the pulverized glycosyl hesperetin, it is treated with the above items (a) to (e) similarly as in the test samples.

<GC/MS Analysis Condition>

GC/MS Analyzer: "Clarus SQ8T GC/MS", commercialized by PerkinElmer, Inc., MA, USA.

Column: VF-WAXms, having a length of 30 m, an inner diameter of 0.25 mm, and a thickness of 0.25 µm, commercialized by Agilent Technologies Inc., CA, USA.

Detector: mass analyzer
Carrier gas: helium gas
Linear velocity: 35 cm/sec

Increasing temperature conditions: Keeping the column temperature at 40° C. for three minutes, increasing the column temperature from 40° C. to 80° C. at a rate of 5° C./min, increasing the column temperature from 80° C. to 200° C. at a rate of 10° C./min, keeping the column temperature at 200° C. for seven minutes, increasing the column temperature from 200° C. to 22° C. at a rate of 10° C./min, and then keeping the column temperature at 220° C. for eight minutes.

Surrogate substance: cyclohexanol, a first grade reagent, commercialized by Katayama Chemical Industries Co., Ltd, Osaka, Japan.

Internal standard substance: heneicosane, a standard substance for GC, commercialized by Tokyo Chemical Industry Co., Ltd., Tokyo, Japan.

Extraction solvent: diethyl ether, a special grade reagent, commercialized by Wako Pure Chemical Industries, Ltd., Osaka, Japan.

<B. Quantification of Furfural in Sample>

A calibration curve was drawn with the data on furfural, as a control, a special grade reagent, commercialized by Wako Pure Chemical Industries, Ltd., Osaka, Japan, determined by GO/MS analysis; based on this, test samples were determined for their furfural contents.

(2) 4-VA Content

Test samples 1 to 8 were respectively determined for their 4-VA contents using the following reagents, protocols, and apparatuses. The measuring method was conducted in accordance with "About benzene in soft drinks" of Notification No. 0728008, as of Jul. 28, 2006, issued by the First Evaluation and Registration Division Chief, Department of Food Safety, Standards and Evaluation Division, Pharmaceutical and Food Safety Bureau, Organization of the Ministry of Health, Labour and Welfare.

<A. Reagents and Preparations of Solutions>

(a) Sodium Chloride, a Specimen for Water Quality Test, Commercialized by Wako Pure Chemical Industries, Ltd., Osaka, Japan.

(b) Preparation of Cyclohexanol Standard Stock Solution

Cyclohexanol, a first grade reagent, commercialized Katayama Chemical Industries, Co., Ltd., Osaka, Japan, was dissolved in methanol for use in general tests, processes and apparatus of Japanese Pharmacopoeia (JP), into 0.01 w/w % cyclohexanol solution (called "cyclohexanol standard stock solution", hereinafter).

(c) Internal Standard Solution

Using the above cyclohexanol standard stock solution and methanol, 0.0004 w/w % cyclohexanol solution (called "internal standard solution 1", hereinafter) and 0.00004 w/w % cyclohexanol solution (called "internal standard solution 2", hereinafter) were prepared.

(d) Preparation of Standard Stock Solution

4-VA, commercialized by Wako Pure Chemical Industries, Ltd., Osaka, Japan, was dissolved in methanol into 0.0005 w/w % 4-VA solution (called "standard solution A", hereinafter) or 0.00005 w/w % 4-VA solution (called "standard solution B", hereinafter).

(e) Preparation of Standard Stock Solution for Calibration Curve

Five different standard stock mixture solutions for calibration curve, having respective 4-VA concentrations of 0.05, 0.1, 0.2, 0.5, and 1.0 µg/mL, were prepared using the above standard solutions A and B, the above internal standard solution 1, and methanol.

(f) Preparation of Standard Solution for Calibration Curve

Five different standard solutions for calibration curve were prepared as follows: Ten milliliter aliquots of ultrapure water were placed in five 20-mL headspace vials, added with 10 µL of any one of the above five different standard stock mixture solutions for calibration curve, and admixed with 3.0 g of sodium chloride, followed by immediately sealing the vials and stirring the content in each vial for dissolution.

Test samples 1 to 8 were respectively, precisely weighed by 0.20 g, d.s.b., placed in eight 20-mL headspace vials, added with ultrapure water to give a total weight of 10.0 g, and stirred for dissolution. To each of the resulting solutions were added 10 µL of the above internal standard solution 2 and 3.0 g of sodium chloride, followed by immediately sealing the vials, dissolving the contents in the vials by stirring to obtain eight different test samples containing any one of test samples 1 to 8.

<C. Quantitative Method for 4-VA>
(a) Measurement Condition
<GC/MS Analysis Condition>
  GC/MS Analyzer: "Clarus SQ8T GC/MS", commercialized by PerkinElmer Co., Ltd., Kanagawa, Japan.
  Head space sampler: "TurboMatrix Trap 40"
  Column: VF-WAXms, having a column length of 30 m, an inner diameter of 0.25 mm, and a membrane thickness of 0.25 µm, commercialized by Agilent Technologies Inc., CA, USA.
  Detector: mass analyzer
  Carrier gas: helium gas
  Linear velocity: 35 cm/sec
  Column injection temperature: 200° C.
  Increasing temperature conditions: Keeping the column temperature at 40° C. for three minutes, increasing the column temperature from 40° C. to 80° C. at a rate of 5° C./min, increasing the column temperature from 80'C to 200° C. at a rate of 10° C./min, keeping the column temperature at 200° C. for seven minutes, increasing the column temperature from 200° C. to 220° C. at a rate of 10° C./min, and then keeping the column temperature at 220° C. for eight minutes.
  Vial oven temperature: 60° C.
  Needle temperature: 140° C.
  Transfer line temperature: 205° C.
  Vial-heating time: 30 min
<Detection Method>
  Ionization (Electron impact (EI)) method
  Selected ion monitoring (SIM)
    m/z 134, 119 (4-VA)
    m/z 82, 57 (cyclohexanol, a first grade specimen, commercialized by Katayama Chemical Industries Co., Ltd, Osaka, Japan)
(b) Quantification of 4-VA Based on the ratio of the peak heights of 4-VA and cyclohexanol as an internal standard for each of the above eight test samples and the five standard mixture solutions for generating a calibration curve, as well as on a separately created 4-VA calibration curve, the test samples 1 to 8 were determined for their 4-VA concentrations to calculate their 4-VA contents.

(3) Color Tone and Coloration Degree

Aqueous solutions of the test samples 1 to 8 were respectively, macroscopically observed their color tone and determined their coloration degree by the following procedures: The test samples 1 to 8 were respectively prepared into 1 w/w % aqueous solutions, and 40 mL of each of which was placed in a 50-mL sealed container and heated at 100° C. for 30 min. Thereafter, each of the resulting solutions was adjusted to 27° C., placed in a cell with a 1-cm width, and measured for absorbances of $OD_{420nm}$ and $OD_{720nm}$ at wavelengths of 420 nm and 720 nm using "UV-2600", a product name of a spectrophotometer, commercialized by Shimadzu Corporation, Kyoto, Japan, followed by determining the difference between the two absorbances ($OD_{420nm}-OD_{720nm}$) for use as a coloration degree.

(4) Electric Conductivity

The test samples 1 to 8 were respectively dissolved in refined water into 1 w/w % aqueous solutions, which were then respectively heated at 100° C. for 30 min in a sealed container, cooled to 20° C., and measured for electric conductivity at 20° C. using "CM-5 AT", a product name of a conductance meter, commercialized by DKK Toa Corporation, Tokyo, Japan.

(5) Content of Ionic Compound

Ionic compounds could not be easily quantified, but they were determined for the contents of cationic metal elements by the following procedure as a facile method: Each of the test samples 1 to 8 was precisely weighed by about 0.5 g in "Falcon Tube", a product name of a 50-mL container, commercialized by Japan, Becton Dickinson and Company, Tokyo, Japan, added with and dissolved in 20 mL of ultrapure water by heating, added with 0.54 mL of 60 w/w % aqueous nitric acid solution for precision assay, heated at 70° C. for 14 hours, cooled to ambient temperature, adjusted to give a total volume of 50 mL with ultrapure water, and quantified for the contents of metal elements using the following analyzer under the conditions below. As a control, a sample consisting of ultrapure water was used.

<Apparatus and Measurement Conditions>
  Inductively coupled plasma emission spectrophotometer: "CIROS-120", commercialized by SPECTRO Analytical Instruments GmbH, Boschstrasse, Germany
  Plasma power: 1,400 W
  Plasma gas (Ar): 13.0 L/min
  Auxiliary gas (Ar): 1.0 L/min
  Nebulizer gas (Ar): 1.0 L/min
  Pump operation: 1.0 mL/min
  Method of calculating the content of metal element (ppm): {(Measured value of test sample)−(Measured value of control)}×Dilution rate
  Table 1 shows the results of the above items (1) to (5). Since the compositions of the glycosyl hesperetins of the test samples 1 to 8 were substantially the same as those which are shown in Examples 1, 3, 4, and 5, they were omitted from the table.

TABLE 1

|  | Test sample | Furfural content (ppb) | 4-VA Content (ppb) | Color tone | Coloration degree ($OD_{420\,nm}-OD_{720\,nm}$) | Electric conductivity (µS/cm) | Content of metal element (ppm) | | | |
|---|---|---|---|---|---|---|---|---|---|---|
|  |  |  |  |  |  |  | Ca | K | Mg | Na |
| Control | 1* | 308 | 40.2 | Pale yellow | 0.24 | 10.59 | 2.948 | 0.172 | 0.464 | 0.975 |
|  | 2 | 322 | 46.6 | Pale yellow | 0.26 | 11.77 | 3.038 | 0.186 | 0.560 | 1.175 |
|  | 3 | 343 | 55.1 | Pale yellow | 0.26 | 10.94 | 3.248 | 0.192 | 0.564 | 1.205 |
|  | 4 | 385 | 63.8 | Pale yellow | 0.26 | 11.46 | 4.538 | 0.242 | 0.732 | 1.205 |

TABLE 1-continued

| Test sample | | Furfural content (ppb) | 4-VA Content (ppb) | Color tone | Coloration degree ($OD_{420\,nm}$-$OD_{720\,nm}$) | Electric conductivity (μS/cm) | Content of metal element (ppm) | | | |
|---|---|---|---|---|---|---|---|---|---|---|
| | | | | | | | Ca | K | Mg | Na |
| Present invention | 5 | 8 | 1.2 | Pale yellow** | 0.15 | 2.86 | 0.374 | 0.039 | 0.052 | 0.072 |
| | 6 | 10 | 1.5 | Pale yellow** | 0.17 | 4.54 | 0.385 | 0.042 | 0.063 | 0.088 |
| | 7 | 11 | 1.8 | Pale yellow** | 0.20 | 6.19 | 0.400 | 0.043 | 0.063 | 0.087 |
| | 8 | 12 | 2.1 | Pale yellow** | 0.20 | 6.59 | 0.455 | 0.050 | 0.077 | 0.092 |

Note:
The symbol "*" means that it is substantially the same as conventional composition containing glycosyl hesperetin prepared by the method in Example for Reference 1.
The symbol "**" means that it has a more pale yellow color tone than those of the test samples 1 to 4 as controls.

As clear from Table 1, all the test samples 1 to 4 had a furfural content of over 300 ppb, while all the test samples 5 to 8 had a content of about 10 ppb. In addition, all the test samples 1 to 4 had a 4-VA content of over 40 ppb, while all the test samples 5 to 8 had a content of about 2 ppb or lower.

Also, as shown in Table 1, the test samples 1 to 4 (Controls) in an aqueous solution form gave a macroscopic color tone of pale yellow, while the test samples 5 to 8 in an aqueous solution form (Present inventions) had an apparently pale yellow tone compared to Controls. All the test samples 1 to 4 in an aqueous solution form had a coloration degree of 0.24 or higher, while all the test samples 5 to 8 in an aqueous solution form had a lower coloration degree of 0.20 or lower. The coloration degrees of the test samples 5 to 8 in an aqueous solution form became lower as the increase of the amount of the reducing agent used.

As clear from Table 1, the test samples 1 to 4 in an aqueous solution form had an electric conductivity of about 11 to about 12 μS/cm as being over 10 μS/cm, while the test samples 5 to 8 in an aqueous solution form had an electric conductivity of about 3 to about 7 μS/cm as being less than 10 μS/cm.

Besides, as clear from Table 1, any one of the contents of the metal elements of calcium, potassium magnesium, and sodium in the test samples 5 to 8 were evidently low compared to the test samples 1 to 4, and the results were well coincided with their measured electric conductivities.

These results revealed that, compared to conventional products, the glycosyl hesperetins of the present invention prepared with the prescribed reducing agents were significantly reduced in furfural content, 4-VA content, and coloration degree, as well as electric conductivity and metal element content.

Experiment 2: Sensory Test

A sensory test as indicated below was conducted with conventional products and the glycosyl hesperetins according to the present invention.
(1) Outline of Sensory Test and Preparation of Test Sample A sensory test shown in the following item (2) was performed with eight healthy panelists, consisting of two females and six males, 28 to 59 years old, by using, as a representative example of the glycosyl hesperetin of the present invention, the test sample 6 which had showed intermediate values for the furfural contents, coloration degrees, electric conductivities, and metal element contents of the test samples 5 to 8 as used in Experiment 1; and, as a representative example of conventional products, the test sample 1 which had showed minimum values in all of the furfural contents, coloration degrees, electric conductivities, and metal element contents of the test samples 1 to 4 as used in Experiment 1. The test sample 1 as a conventional product and the test sample 6 as the glycosyl hesperetin of the present invention were respectively dissolved at ambient temperature in RO water, obtained through a reverse osmosis membrane, for use as unheated the test samples 1 and 6, respectively, which were then stored in sealed containers until being subjected to the following test. While, the test samples 1 and 6 without heating (called "unheated test samples 1 and 6", hereinafter) were respectively placed in a container, sealed therein, heated in a boiling water bath for 30 min (called "heat treatment", hereinafter), and then cooled to ambient temperature for use as test samples 1 and 6 with heat treatment (called "heated test samples 1 and 6", hereinafter).
(2) Sensory Test Each panelist was asked to individually evaluate (a) coloration and (b) odor of 10-mL aliquots of the unheated test samples 1 and 6 and the heated test samples 1 and 6, all of which had been obtained in the above item (1) and adjusted to give an ambient temperature before tasting them. Thereafter, each panelist was allowed to gargle with plain boiled water before tasting each test sample and allowed to individually evaluate (c) bitterness (including roughness, harshness, or astringency), (d) aftertaste, and (e) odor when tasting. Each panelist was asked to evaluate the unheated and heated test samples 1 and 6 for the evaluation items (a) to (e), wherein an evaluation standard was as shown in the following Table 2, in which the term "conventional product" means "the test sample 1", and the unheated test sample 1 and the heated test sample 1 were respectively provided as controls for the unheated test sample 6 and the heated test sample 6, respectively. The results are respectively in Tables 3 and 4.

Evaluation Standard:

TABLE 2

| | | | Evaluation score (judged on 5-point evaluation scale) |
|---|---|---|---|
| Before tasting | (a) Coloration | Comparison to conventional products | 1: Distinctly low<br>2: Slightly low<br>3: Comparable<br>4: Slightly high<br>5: Distinctly high |
| | (b) Odor | Comparison to conventional products | 1: Distinctly weak<br>2: Slightly weak<br>3: Comparable |

TABLE 2-continued

|  |  |  | Evaluation score (judged on 5-point evaluation scale) |
|---|---|---|---|
| When tasting | (c) Bitterness | Comparison to conventional products | 4: Slightly sharp<br>5: Distinctly sharp<br>1: Distinctly preferable<br>2: Slightly preferable<br>3: Undecided<br>4: Rather unfavorable<br>5: Distinctly unfavorable |
|  | (d) Aftertaste | Comparison to conventional products | 1: Distinctly preferable<br>2: Slightly preferable<br>3: Undecided<br>4: Rather unfavorable<br>5: Distinctly unfavorable |
|  | (e) Odor | Comparison to conventional products | 1: Distinctly weak<br>2: Slightly weak<br>3: Comparable<br>4: Slightly sharp<br>5: Distinctly sharp |

(3) Result of Sensory Test

TABLE 3

Score distribution of the unheated test sample 6:

| | Number of panelists | | | | |
|---|---|---|---|---|---|
| | Before tasting | | When tasting | | |
| Score | (a) Coloration | (b) Odor | (c) Bitterness | (d) Aftertaste | (e) Odor |
| 1 | 4 | 3 | 0 | 3 | 4 |
| 2 | 4 | 5 | 7 | 4 | 4 |
| 3 | 0 | 0 | 1 | 1 | 0 |
| 4 | 0 | 0 | 0 | 0 | 0 |
| 5 | 0 | 0 | 0 | 0 | 0 |

TABLE 4

Score distribution of the heated test sample 6:

| | Number of panelists | | | | |
|---|---|---|---|---|---|
| | Before tasting | | When tasting | | |
| Score | (a) Coloration | (b) Odor | (c) Bitterness | (d) Aftertaste | (e) Odor |
| 1 | 6 | 4 | 3 | 4 | 5 |
| 2 | 2 | 3 | 4 | 1 | 1 |
| 3 | 0 | 1 | 1 | 3 | 2 |
| 4 | 0 | 0 | 0 | 0 | 0 |
| 5 | 0 | 0 | 0 | 0 | 0 |

The evaluation results in Tables 3 and 4 do not show the evaluation results of (a) coloration, (b) odor, (c) bitterness, (d) aftertaste, and (e) odor for the conventional product (the heated/unheated test sample 1 as a control) per se; however, as indicated in the evaluation standard, the evaluation results in Tables 3 and 4 were for the glycosyl hesperetin of the present invention evaluated based on those of the conventional product, and therefore the evaluation results of the conventional products correspond to the midpoint of "3" for each score, evaluated based on 5-point evaluation scale, shown in the evaluation standard.

By contrast, as clear from the evaluation results in Table 3, the unheated test sample 6, i.e., the glycosyl hesperetin of the present invention without heat treatment gave the numbers of panelists, who had judged as "1-point" as the highest score on the 5-point evaluation scale for the evaluation items of (a) coloration, (b) odor, (c) bitterness, (d) aftertaste, and (e) odor, to be four, three, zero, three, and four (14 subjects in total), respectively, each among the eight panelists. While, the heated test sample 6 shown in the evaluation results in Table 4, i.e., the glycosyl hesperetin of the present invention with heat treatment had the numbers of panelists, who had judged as "1-point" as the highest score in the 5-point evaluation scale for the evaluation items of (a) coloration, (b) odor, (c) bitterness, (d) aftertaste, and (e) odor, to be four, five, seven, four, and four (24 subjects in total), each among the eight panelists, respectively. These results indicate that the glycosyl hesperetin of the present invention is a relatively high-quality glycosyl hesperetin that is effectively reduced in odor, as well as in miscellaneous tastes and coloration, compared to conventional products.

Similarly, as clear from the evaluation results in Table 3, the unheated test sample 6, i.e., the glycosyl hesperetin of the present invention without heat treatment gave the numbers of panelists, who had judged as "4-point" as being 1-point higher than the lowest level of 5-point upon the 5-point evaluation scale for the evaluation items of (a) coloration, (b) odor, (c) bitterness, (d) aftertaste, and (e) odor, were respectively all zero (zero in total) While, as clear from the evaluation results in Table 4, the heated test sample 6, i.e., the glycosyl hesperetin of the present invention with heat treatment gave the numbers of panelists, who had judged "4-point" as being 1-point higher than the lowest level of 5-point upon the 5-point evaluation scale for the evaluation items of (a) coloration, (b) odor, (c) bitterness, (d) aftertaste, and (e) odor, were respectively all zero (zero in total) These results show that the glycosyl hesperetin of the present invention is a relatively high-quality glycosyl hesperetin that is effectively reduced in odor, as well as in miscellaneous tastes and coloration, compared to conventional products.

Based on these results, compared to conventional products, the glycosyl hesperetin of the present invention, regardless of its heated or unheated treatment, is distinctly advantageous in terms of all the evaluation items of (a) coloration, (b) odor, (c) bitterness, (d) aftertaste, and (e) odor, wherein the difference in quality between the heated and unheated glycosyl hesperetins becomes more distinct when they are heated.

When subjected to a sensory test similar to "(2) Sensory test" as in the above-mentioned Experiment 2, the test samples 5, 7, and 8, which are shown in "(1) Preparation of test sample" as in Experiment 2, gave substantially the same results as in the above test sample 6.

Thus, it was revealed that the glycosyl hesperetin of the present invention is significantly reduced in bitterness including harsh taste, bitter taste, astringent taste, and aftertaste; or it is significantly reduced in miscellaneous taste and distinctly reduced in coloration. Also, it was revealed that the glycosyl hesperetin is distinctly reduced in odor compared to conventional products.

Experiment 3: Relationship Between (a) the Miscellaneous Tastes and Coloration of Glycosyl Hesperetin and (b) the Contents of Furfural and 4-VA The following tests were carried out to examine the relationship between (a) the miscellaneous tastes and coloration of glycosyl hesperetin and (b) the contents of furfural and 4-VA.

(1) Preparation of Test Sample

In accordance with the methods in the later described Example 4 and Example for Reference 1, a sample for the glycosyl hesperetin of the present invention (called "Sample A", hereinafter) and another sample as a representative of conventional products (called "Sample B", hereinafter). For convenience, Samples A and B were mixed in appropriate ratios to obtain three types of glycosyl hesperetin samples with stepwisely different furfural contents (called "test samples 9 to 11") as shown in Table 5.

(2) Contents of Furfural and 4-VA

The contents of furfural and 4-VA in the test samples 9 to 11 were respectively determined according to the measuring methods shown in (1) and (2) in Experiment 1.

(3) Judgment Test on Coloration

Nine healthy females and males, consisting of two females and seven males, 28 to 57 years old, as panelists, were subjected to an evaluation test on coloration using the test samples 9 to 11 and sample B (called "Control", hereinafter). These test samples 9 to 11 and Control were respectively dissolved in distilled water at ambient temperature into 1 w/w % aqueous solutions, which were then macroscopically observed and judged by the panelists as follows: It was judged as "Judgement A1", when the solution(s) was/were evaluated and judged by the panelists as "being reduced in coloration" compared to control; and it was judged as "Judgement B1", when the solution(s) was/were evaluated and judged as "being reduced in coloration". The results are in Table 5.

(4) Sensory Test

The above nine females and males as panelists were subjected to a sensory test on the miscellaneous tastes of the aforesaid test samples 9 to 11 and Control. These test samples 9 to 11 and Control were respectively dissolved in distilled water at ambient temperature into 1 w/w % aqueous solutions, which were then drunken by the panelists and judged by them as "Judgement A2" when the aqueous solution(s) was/were evaluated as "being improved in miscellaneous tastes", and judged as "Judgement B2" when the solution(s) was/were evaluated as "being not improved in miscellaneous tastes". The results are in Table 5.

TABLE 5

| Test sample | Furfural content (ppb) | 4-VA Content (ppb) | Number of panelists | | | |
|---|---|---|---|---|---|---|
| | | | Judgment test on coloration | | Sensory test | |
| | | | Judgement A1 | Judgement B1 | Judgement A2 | Judgement B2 |
| Sample B (Control) | 330 | 45.0 | | | | |
| 9 | 234 | 39.4 | 4 | 5 | 4 | 5 |
| 10 | 171 | 21.9 | 9 | 0 | 8 | 1 |
| 11 | 108 | 10.2 | 9 | 0 | 9 | 0 |
| Sample A | 56 | 2.0 | | | | |

Note:
"Judgement A1" and "Judgement B1" mean that, in the judgement test on coloration, the panelist(s) evaluated a test sample as "being reduced in coloration" and "being not reduced in coloration" compared to Control, respectively. While, "Judgement A2" and "Judgement B2" mean that, in the sensory test, the panelist(s) evaluated a test sample as "being improved in miscellaneous tastes" and "being not improved in miscellaneous tastes" compared to Control, respectively.

As clear from the results in Table 5, the miscellaneous tastes of glycosyl hesperetins were distinctly and significantly improved at the furfural content of around 200 ppb as a border and were distinctly and significantly improved at the 4-VA content of around 30 ppb as another border. The same applied to the coloration of glycosyl hesperetins. These results strongly suggested that the furfural content and the 4-VA content can be used as indexes for surely distinguishing glycosyl hesperetins that are significantly reduced in miscellaneous tastes and distinctly reduced in coloration in such a manner of selecting the ones with a furfural content of not higher than 200 ppb and a 4-VA content of not higher than 30 ppb for obtaining desired glycosyl hesperetins that are significantly reduced in miscellaneous tastes and distinctly reduced in coloration compared to conventional products.

The following Table 6 shows the relationship between (a) the miscellaneous tastes of different particulate glycosyl hesperetins and (b) the contents of furfural and 4-VA as disclosed in the aforementioned Table 1 in Experiment 1, the later described. Examples 1 to 7, and Example for Reference 1. In Table 6, the test samples 5 to 8 as the glycosyl hesperetins of the present invention and the pulverized glycosyl hesperetins in Examples 1 to 7 (called "the present test samples" all together, hereinafter) had furfural contents of not higher than 191 ppb and 4-VA contents of not higher than 28.7 ppb, meaning that the present test samples were significantly reduced in the miscellaneous tastes characteristic of conventional products. On the contrary, the test samples 1 to 4 and the pulverized glycosyl hesperetin in Example for Reference 1 as Controls 1 to 5 (called "control test samples" all together, hereinafter) had furfural contents of 308 ppb or higher and 4-VA contents of 40.0 ppb or higher, and they all had the miscellaneous tastes characteristic of conventional products.

The results of these Experiments, Examples, and Example for Reference summarized in the following Table 6 were well coincided with the results in Experiment 3; and based on these results, it can be judged that the selection of glycosyl hesperetins with a furfural content of less than 200 ppb and/or a 4-VA content of less than 30 ppb, which is made by using the furfural content and/or the 4-VA content as indexes, results in an obtention of the desired glycosyl hesperetins that are significantly reduced in miscellaneous tastes compared to conventional products.

TABLE 6

| | Test sample | Furfural content (ppb) | 4-VA Content (ppb) | Miscellaneous taste |
|---|---|---|---|---|
| Control 1 | 1* | 308 | 40.2 | x |
| Control 2 | 2* | 322 | 46.6 | x |
| Control 3 | 3* | 343 | 55.1 | x |
| Control 4 | 4* | 385 | 63.8 | x |
| Control 5 | Example for Reference 1 | 310 | 40.0 | x |
| Present invention | Example 7 | 191 | 28.7 | o |
| Present invention | Example 6 | 180 | 20.0 | o |
| Present invention | 8* | 12 | 2.1 | o |
| Present invention | Example 1 | 12 | 2.0 | o |
| Present invention | 7* | 11 | 1.8 | o |
| Present invention | Example 2 | 11 | 1.5 | o |
| Present invention | Example 3 | 10 | 3.0 | o |
| Present invention | 6* | 10 | 1.5 | o |
| Present invention | Example 5 | 10 | 1.5 | o |

TABLE 6-continued

| Test sample | | Furfural content (ppb) | 4-VA Content (ppb) | Miscellaneous taste |
|---|---|---|---|---|
| Present invention | Example 4 | 9 | 2.0 | o |
| Present invention | 5* | 8 | 1.2 | o |

Note:
In the table, the test samples affixed with the symbol "*" are cited from Table 1 in the specification. Those with the symbols "o" and "x" mean that the miscellaneous tastes characteristic of conventional products are significantly reduced and that the miscellaneous tastes characteristic of conventional products are still remained, respectively.

From the aforesaid Experimental results, since the glycosyl hesperetins of the present invention are significantly reduced in miscellaneous tastes and distinctly reduced in coloration and odor compared to conventional products, they per se are quite advantageously useful as food products that are significantly reduced in miscellaneous tastes and distinctly reduced in coloration and odor, and they have become useful without any inconvenience even when used in food products, luxury grocery items, cosmetics, pharmaceuticals such as susceptive diseases, quasi-drugs, chemicals, industrial feedstock and materials, feeds, baits, clothes, sundries including commodities, plastic products, etc., in which conventional products could not have been used due to their miscellaneous tastes alone or along with their coloration, as well as their odor; or in which deterioration is inevitably induced.

The following explain the present invention in more detail with reference to Examples and Example for Reference but they should never limit the scope of the present invention.

Example 1

<Particulate Glycosyl Hesperetin>

Four parts by mass of 1 N aqueous sodium hydroxide solution was heated to 80° C. and added with one part by mass of hesperidin and seven parts by mass of dextrin (dextrose equivalent (DE) of 20), followed by dissolving the contents in the mixture under stirring conditions for 30 min, adjusting the solution to pH 9.0, adding 30 units/g dextrin of a CGTase, derived from *Geobacillus stearothermophilus* Tc-91 strain (FERM BP-11273) deposited on Jul. 30, 1973, and applied for International Patent Organism Depositary in National Institute of Advanced Industrial Science and Technology, Tsukuba Central 6, 1-1, Higashi 1-chome, Tsukuba-shi, Ibaraki-ken, 305-8566 Japan, and subjected to an enzymatic reaction for 18 hours while keeping the pH at 6.9 and the temperature at 50° C. to convert about 70% of hesperidin into α-glycosyl hesperidin. To the resulting enzymatic reaction solution was added 0.05% of sodium pyrosulfite as a reducing agent, followed by heating the solution at 100° C. for 30 min, inactivating the remaining enzyme in the solution, adding "GLUCOZYME", a product name of a glucoamylase, commercialized by Nagase ChemteX Corporation, Osaka, Japan, in an amount of 100 units per gram solids of the enzymatic reaction solution, and enzymatically reacting the resulting mixture for five hours while keeping the pH at 5.0 and the temperature at 55° C. to form α-glucosyl hesperidin. The resulting enzymatic reaction solution was heated to inactivate the remaining enzyme and filtered, followed by feeding the resulting filtrate to a column packed with "DIAION HP-10", a product name of a porous synthetic adsorbent, commercialized by Mitsubishi Chemical Corporation, Tokyo, Japan, at a space velocity (SV) of two. As a result, α-glucosyl hesperidin and intact hesperidin in the solution were adsorbed on the porous synthetic adsorbent, but the remaining D-glucose, salts, and the like were eluted out from the column without adsorption. Thereafter, the column was fed with refined water for washing and further fed with an aqueous ethanol solution while increasing stepwisely the concentration of ethanol to collect fractions containing α-glucosyl hesperidin, followed by pooling the fractions, concentrating the pooled fractions in vacuo, and pulverizing the concentrate to obtain a pale yellow particulate glycosyl hesperetin in a yield of about 70%, d.s.b., to the solid mass of the material hesperidin. The resulting particulate glycosyl hesperetin contained 80.0% of α-glucosyl hesperidin, 12.3% of hesperidin, and 7.7% of other ingredients.

The product thus obtained had a furfural content of 12 ppb, 4-VA content of 2 ppb, coloration degree of 0.19, and electric conductivity of about 6 µS/cm. Also, the product contained calcium, potassium, magnesium, and sodium in respective amounts of about 0.4 ppm, about 0.05 ppm, about 0.1 ppm, and about 0.1 ppm.

Compared to conventional products, the above product has advantageously characteristic features: It is significantly reduced in miscellaneous tastes and distinctly reduced in coloration and odor, and the miscellaneous tastes are significantly reduced and the coloration and odor are also effectively, distinctly decreased even when heated for 30 min under a relatively high temperature condition of 90 to 100° C. Accordingly, food products, cosmetics, pharmaceuticals such as agents for susceptive diseases, quasi-drugs, chemicals, industrial feedstock and materials, feeds, baits, clothes, sundries including commodities, or plastic products, all of which, containing the product, are significantly reduced in miscellaneous tastes and distinctly reduced in coloration and odor as advantageous benefits, even when kept or stored at a temperature within or below the above temperature range for several tens of minutes through several months, compared to the case of using conventional products. Similar to conventional products, the product can be advantageously used as a vitamin P-enriched agent, as well as a highly-safe natural anti-oxidant, stabilizer, quality-improving agent, preventive, therapeutic agent, or ultraviolet-absorbing agent in various compositions such as food products, luxury grocery items, feeds, baits, cosmetics, pharmaceuticals such as agents for susceptive diseases, quasi-drugs, chemicals, industrial feedstock and materials, feeds, baits, clothes, sundries including commodities, plastic products, etc.

Example 2

<Particulate Glycosyl Hesperetin>

Four parts by mass of 1 N aqueous sodium hydroxide solution was heated to 80° C. and, while keeping the temperature, the solution was successively added with one part by mass of hesperidin, four parts by mass of dextrin (DE 10), and 0.06 part by mass of sodium sulfite, followed by dissolving the contents in the mixture while stirring for 30 min, neutralizing the solution with 0.01 N hydrochloric acid solution, adding 20 units/g dextrin of a CGTase, derived from *Geobacillus stearothermophilus* Tc-91 strain (FERM BP-11273) deposited for International Patent Organism Depositary in National Institute of Advanced Industrial Science and Technology, Tsukuba Central 6, 1-1, Higashi 1-chome, Tsukuba-shi, Ibaraki-ken, 305-8566 Japan, and keeping the mixture at pH 6.0 and 75° C. for 24 hours under stirring conditions to effect an enzymatic reaction. The resulting enzymatic reaction solution was sampled for analysis on high-performance liquid chromatography (HPLC), revealing that about 69% of hesperidin was converted to α-glycosyl hesperidin. The enzymatic reaction solution was added with sodium pyrosulfite as a reducing agent to give a concentration of 0.03%, heated at 90° C. for 120 min, added with 50 units/g of the above intermediate product containing α-glycosyl hesperidin, and subjected to an enzymatic reaction for 10 hours while keeping the pH at 5.0 and the temperature at 55° C. to form α-glucosyl hesperidin. The resulting enzymatic reaction solution was heated to inactivate the remaining enzyme and filtered, followed by feeding the resulting filtrate to a column packed with "DIAION HP-10", a product name of a porous synthetic adsorbent, commercialized by Mitsubishi Chemical Corporation, Tokyo, Japan, at SV 2. As a result, α-glucosyl hesperidin and intact hesperidin in the solution were adsorbed on the porous synthetic adsorbent, but the remaining saccharides, salts, and the like were eluted out from the column without adsorption. Thereafter, the column was fed with refined water for washing and further fed with an aqueous ethanol solution while increasing stepwise the concentration of ethanol to collect fractions containing α-glucosyl hesperidin, followed by pooling the fractions, concentrating the pooled fractions in vacuo, and pulverizing the concentrate to obtain a pale yellow particulate glycosyl hesperetin in a yield of about 68%, d.s.b., to the solid mass of the material hesperidin. The resulting particulate glycosyl hesperetin contained 77.0% of α-glucosyl hesperidin, 15.5% of hesperidin, and 7.5% of other ingredients.

The product thus obtained had a furfural content of 11 ppb, 4-VA content of 1.5 ppb, coloration degree of 0.14, and electric conductivity of about 4 µS/cm. Also, the product contained calcium, potassium, magnesium, and sodium in respective amounts of about 0.4 ppm, about 0.06 ppm, about 0.1 ppm, and about 0.1 ppm.

Compared to conventional products, the above product has advantageously characteristic features: It is significantly reduced in miscellaneous tastes and distinctly reduced in coloration and odor, and the miscellaneous tastes thereof are significantly reduced and the coloration and odor are effectively, distinctly decreased even when heated for 30 min under a relatively high temperature condition of 90 to 100° ° C. Accordingly, food products, cosmetics, pharmaceuticals such as susceptive diseases, quasi-drugs, chemicals, industrial feedstock and materials, feeds, baits, clothes, sundries including commodities, or plastic products, all of which, containing the product, are significantly reduced in miscellaneous tastes and distinctly reduced in coloration and odor as advantageous benefits, when kept or stored at a temperature within or below the above temperature range for several tens of minutes through several months, as compared with conventional products. Similar to conventional products, the product can be advantageously used as a vitamin P-enriched agent, as well as a highly-safe natural anti-oxidant, stabilizer, quality-improving agent, preventive, therapeutic agent, or ultraviolet-absorbing agent in various compositions such as food products, luxury grocery items, cosmetics, pharmaceuticals such as susceptive diseases, quasi-drugs, chemicals, industrial feedstock and materials, feeds, baits, clothes, sundries including commodities, plastic products, etc.

Example 3

<Particulate Glycosyl Hesperetin>

Four parts by mass of 1 N aqueous sodium hydroxide solution was heated to 80° C. and, while keeping the temperature, the solution was successively added with 0.1 part by mass of sodium sulfite, one part by mass of hesperidin, and four parts by mass of dextrin (DE 10), followed by dissolving the contents in the mixture while stirring for 30 min, neutralizing the resulting solution with 0.01 N hydrochloric acid solution, promptly adding 20 units/g dextrin of a CGTase, derived from *Geobacillus stearothermophilus* Tc-91 strain (FERM BP-11273) deposited for International Patent Organism Depositary in National Institute of Advanced Industrial Science and Technology, Tsukuba Central 6, 1-1, Higashi 1-chome, Tsukuba-shi, Ibaraki-ken, 305-8566 Japan, and keeping the mixture at pH 6.0 and 75° C. for 24 hours under stirring conditions to effect an enzymatic reaction, whereby about 72% of hesperidin was converted to n-glycosyl hesperidin. The enzymatic reaction solution thus obtained was heated to inactivate the remaining enzyme and filtered, followed by feeding the resulting filtrate to a column packed with "DIAION HP-20", a product name of a porous synthetic adsorbent, commercialized by Mitsubishi Chemical Corporation, Tokyo, Japan, at SV 2. As a result, α-glycosyl hesperidin and intact hesperidin in the solution were adsorbed on the porous synthetic adsorbent, but the remaining D-glucose, salts, and the like were eluted out from the column without adsorption. Thereafter, the column was fed with refined water for washing and further fed with an aqueous ethanol solution while increasing stepwise the concentration of ethanol to collect fractions containing α-glycosyl hesperidin, followed by pooling the fractions, concentrating the pooled fractions in vacuo, and pulverizing the concentrate to obtain a pale yellow particulate glycosyl hesperetin in a yield of about 71%, d.s.b., to the solid mass of the material hesperidin. The particulate glycosyl hesperetin thus obtained contained 76.0% of α-glycosyl hesperidin, 18.5% of hesperidin, and 5.5% of other ingredients.

The product thus obtained had a furfural content of 10 ppb, 4-VA content of 3.0 ppb, coloration degree of 0.17, and electric conductivity of about 4 µS/cm. Also, the product contained calcium, potassium, magnesium, and sodium in respective amounts of about 0.3 ppm, about 0.04 ppm, about 0.1 ppm, and about 0.05 ppm.

Compared to conventional products, the above product has advantageously characteristic features: It is significantly reduced in miscellaneous tastes and distinctly reduced in coloration and odor, and the miscellaneous tastes thereof are significantly reduced and the coloration and odor are effectively, distinctly decreased even when heated for 30 min under a relatively high temperature condition of 90 to 100° C. Accordingly, food products, cosmetics, pharmaceuticals such as susceptive diseases, quasi-drugs, chemicals, industrial feedstock and materials, feeds, baits, clothes, sundries including commodities, or plastic products, all of which, containing the product, are significantly reduced in miscellaneous tastes and distinctly reduced in coloration and odor as advantageous benefits, when kept or stored at a temperature within or below the above temperature range for several tens of minutes through several months, compared to conventional products. Similar to conventional products, the product can be advantageously used as a vitamin P-enriched agent, as well as a highly-safe natural anti-oxidant, stabilizer, quality-improving agent, preventive, therapeutic agent, or ultraviolet-absorbing agent in various compositions such as food products, luxury grocery items, cosmetics, pharmaceuticals such as anti-susceptive diseases, quasi-drugs, chemicals, industrial feedstock and materials, feeds, baits, clothes, sundries including commodities, plastic products, etc.

Example 4

<Particulate Glycosyl Hesperetin>

One part by mass of hesperidin, 10 parts by mass of dextrin (DE 8), and 0.05 part by mass of sodium pyrosulfite as a reducing agent were added to 50 parts by mass of water. The resulting mixture was heated at pH 9.5 and 90° C. for 70 min, added with 30 units/g dextrin of a CGTase, derived from *Geobacillus stearothermophilus* Tc-91 strain (FERM BP-11273) deposited for International Patent Organism Depositary in National Institute of Advanced Industrial Science and Technology, Tsukuba Central 6, 1-1, Higashi 1-chome, Tsukuba-shi, Ibaraki-ken, 305-8566 Japan, kept for 40 hours while keeping the pH at 8.2 and the temperature at 65° C. under stirring conditions, added with sodium pyrosulfite as a reducing agent to give 0.05% to the enzymatic reaction solution just before the completion of the enzymatic reaction, heated at 85° C. to inactivate the remaining enzyme, added with 100 units/g solids of the solution of "GLUCOZYME", a glucoamylase specimen, commercialized by Nagase ChemteX Corporation, Osaka, Japan, and reacted for five hours while keeping the pH at 5.0 and the temperature at 55° C. to form α-glucosyl hesperidin. The enzymatic reaction solution thus obtained was heated to inactive the remaining enzyme. The resulting enzymatic reaction solution was added with 0.5 part by weight of "SOLUBLE HESPERIDINASE <Tanabe> No. 2", a hesperidinase preparation, commercialized by Mitsubishi Tanabe Pharma Corporation, Osaka, Japan, adjusted to pH 4, and subjected to an enzymatic reaction at 55° C. for 24 hours. The resulting enzymatic reaction solution was added with 0.01 part by mass of sodium pyrosulfite, heated to inactivate the remaining enzyme, and filtered, followed by feeding the filtrate to a column packed with "DIAION HP-10", a product name of a porous synthetic adsorbent, commercialized by Mitsubishi Chemical Corporation, Tokyo, Japan, at SV 2. As a result, α-glucosyl hesperidin, 7-O-β-glucosyl hesperetin, and intact hesperidin in the solution were adsorbed on the porous synthetic adsorbent, but the remaining D-glucose, salts, and the like were eluted out from the column without adsorption. Thereafter, the column was fed with refined water for washing and further fed with an aqueous ethanol solution while increasing stepwise the concentration of ethanol to collect fractions containing α-glucosyl hesperidin, followed by pooling the fractions, concentrating the pooled fractions in vacuo, and pulverizing the concentrate to obtain a pale yellow particulate glycosyl hesperetin in a yield of about 70%, d.s.b., to the solid mass of the material hesperidin. The particulate glycosyl hesperetin thus obtained contained 81.9% of α-glucosyl hesperidin, 0.5% of hesperidin, 8.9% of 7-O-β-glucosyl hesperetin, and 8.7% of other ingredients.

The product thus obtained had a furfural content of 9 ppb, 4-VA content of 2.0 ppb, coloration degree of 0.16, and electric conductivity of about 4 μS/cm. Also, the product, contained calcium, potassium, magnesium, and sodium in respective amounts of about 0.3 ppm, about 0.03 ppm, about 0.05 ppm, and about 0.05 ppm.

Compared to conventional products, the above product has advantageously characteristic features: It is significantly reduced in miscellaneous tastes and distinctly reduced in coloration and odor, and also the miscellaneous tastes are significantly reduced and the coloration and odor are effectively, distinctly decreased even when heated for 30 min under a relatively high temperature condition of 90 to 100° C. Accordingly, food products, cosmetics, pharmaceuticals such as susceptive diseases, quasi-drugs, chemicals, industrial feedstock and ingredients, feeds, baits, clothes, sundries including commodities, or plastic products, all of which, containing the product, are significantly reduced in miscellaneous tastes and distinctly reduced in coloration and odor as advantageous benefits, when kept or stored at a temperature within or below the above temperature range for several tens of minutes through several months, compared to those with conventional products. Similar to conventional products, the product can be advantageously used as a vitamin P-enriched agent, as well as a highly-safe natural antioxidant, stabilizer, quality-improving agent, preventive, therapeutic agent, or ultraviolet-absorbing agent in various compositions such as food products, luxury grocery items, cosmetics, pharmaceuticals such as anti-susceptive diseases, quasi-drugs, chemicals, industrial feedstock and ingredients, feeds, baits, clothes, miscellaneous goods including daily necessaries, plastic products, etc.

Example 5

<Particulate Glycosyl Hesperetin>

Fifty parts by mass of hesperidin and one part by mass of sodium hyposulfite as a reducing agent were dissolved by heating in 90 parts by mass of 0.25 N aqueous sodium hydroxide solution at 80° C. One hundred and fifty parts by mass of dextrin with DE 8 was added to and dissolved in the above solution, followed by adjusting the resulting solution to pH 9.0, adding 15 units of a CGTase, derived from *Geobacillus stearothermophilus* Tc-91 strain (FERM BP-11273) deposited for International Patent Organism Depositary in National institute of Advanced Industrial Science and Technology, Tsukuba Central 6, 1-1, Higashi 1-chome, Tsukuba-shi, Ibaraki-ken, 305-8566 Japan, to the solution per one part by mass of the dextrin, adjusting the mixture to pH 8.3 while heating it up to 60° C., and subjecting the resulting mixture to an enzymatic reaction for six hours. Thereafter, the reaction mixture was adjusted to pH 7.0, heated to 68° C., and enzymatically reacted for 40 hours. After completion of the enzymatic reaction, the resulting enzymatic reaction mixture was heated to inactivate the remaining enzymes and filtered to obtain an enzymatic reaction solution. An HPLC analysis of the enzymatic reaction solution revealed that 72% of hesperidin in the solution before the enzymatic reaction was converted to α-glucosyl hesperidin and the remaining 28% hesperidin still remained intact. The enzymatic reaction solution was admixed with two parts by mass of "Soluble hesperidinase <TANABE> 2", a product name of hesperidinase as α-L-rhamnosidase, commercialized by Tanabe Seiyaku Co., Ltd., Tokyo, Japan, adjusted to pH 4, enzymatically reacted at 55° C. for 24 hours, added with one part by mass of "GLUCOZYME", a product name of a glucoamyalse, commercialized by Nagase ChemteX Corporation, Osaka, Japan, and further enzymatically reacted at 55° C. for 24 hours. After completion of the enzymatic reaction, the resulting enzymatic reaction solution was heated to inactivate the remaining enzymes, fed to a column packed with "AMBERLITE XAD-7", a product name of a porous adsorbing resin with a medium-polarity, commercialized by Rohm & Hass Company, Philadelphia, USA., followed, by washing the column with water, and eluting out ingredients adsorbed on the resin with 80 v/v % aqueous ethanol solution. After removing ethanol in the eluate, the resulting eluate was freeze dried to obtain a particulate glycosyl hesperetin containing 82.0% of α-glucosyl hesperidin, 8.0% of 7-O-β-glucosyl hesperetin, 1.0% of hesperidin, and 9.0% of other ingredients.

The product thus obtained had a furfural content of 10 ppb, 4-VA content of 1.5 ppb, coloration degree of 0.15, and electric conductivity of less than 10 µS/cm. Also, the product contained calcium, potassium, magnesium, and sodium in respective amounts of about 0.4 ppm, about 0.04 ppm, about 0.1 ppm, and about 0.2 ppm.

Compared to conventional products, the above product has advantageously characteristic features: it is significantly reduced in miscellaneous tastes and distinctly reduced in coloration and odor, and also the miscellaneous tastes are significantly reduced and the coloration and odor are effectively, distinctly decreased even after heated for 30 min under a relatively high temperature condition of 90 to 100° C. Accordingly, food products, cosmetics, pharmaceuticals such as susceptive diseases, quasi-drugs, chemicals, industrial feedstock and ingredients, feeds, baits, clothes, sundries including commodities, or plastic products, all of which, containing the product, are significantly reduced in miscellaneous tastes and distinctly reduced in coloration and odor as advantageous benefits, when kept or stored at a temperature within or below the above temperature range for several tens of minutes through several months, compared to those with conventional products. Similar to conventional products, the product can be advantageously used as a vitamin P-enriched agent, as well as a highly-safe natural anti-oxidant, stabilizer, quality-improving agent, preventive, therapeutic agent, or ultraviolet-absorbing agent in various compositions such as food products, luxury grocery items, cosmetics, pharmaceuticals such as anti-susceptive diseases, quasi-drugs, chemicals, industrial feedstock and ingredients, feeds, baits, clothes, sundries including commodities, plastic products, etc.

Example 6

<Particulate Glycosyl Hesperetin>

Except for adding 0.001% of potassium hyposulfite as a reducing agent to an enzymatic reaction solution, a pale yellow particulate glycosyl hesperetin was obtained similarly as in Example 1 in a yield of about 69%, d.s.b., against the solid mass of the material hesperidin. The particulate glycosyl hesperetin contained 79.5% of α-glucosyl hesperidin, 13.8% of hesperidin, and 6.7% of other ingredients.

The product thus obtained had a furfural content of 180 ppb, 4-VA content of 20 ppb, coloration degree of 0.23, and electric conductivity of less than 10 µS/cm. Also, the product contained calcium, potassium, magnesium, and sodium in respective amounts of about 0.5 ppm, about 0.08 ppm, about 0.1 ppm, and about 0.3 ppm.

Although being inferior to the particulate glycosyl hesperetins obtained in Examples 1 to 5, the above product has advantageous characteristic features compared to conventional products: It is significantly reduced in miscellaneous tastes and distinctly reduced in coloration and odor, and also the miscellaneous tastes are significantly reduced and the coloration and odor are effectively, distinctly decreased even after heated for 30 min under a relatively high temperature condition of 90 to 100° C. Accordingly, food products, cosmetics, pharmaceuticals such as susceptive diseases, quasi-drugs, chemicals, industrial feedstock and ingredients, feeds, baits, clothes, sundries including commodities, or plastic products, all of which, containing the product, are significantly reduced in miscellaneous tastes and distinctly reduced in coloration and odor as advantageous benefits, when kept or stored at a temperature within or below the above temperature range for several tens of minutes through several months, compared to those with conventional products. Similar to conventional products, the product can be advantageously used as a vitamin P-enriched agent, as well as a highly-safe natural anti-oxidant, stabilizer, quality-improving agent, preventive, therapeutic agent, or ultraviolet-absorbing agent in various compositions such as food products, luxury grocery items, cosmetics, pharmaceuticals such as susceptive diseases, quasi-drugs, chemicals, industrial feedstock and ingredients, feeds, baits, clothes, sundries including commodities, plastic products, etc.

Example 7

<Particulate Glycosyl Hesperetin>

Except for replacing the potassium hyposulfite with sodium hydrogen sulfite, a pale yellow particulate glycosyl hesperetin was obtained similarly as in Example 6 in a yield of about 65%, d.s.b., against the solid mass of the material hesperidin. The particulate glycosyl hesperetin thus obtained contained 77.2% of α-glucosyl hesperidin, 16.5% of hesperidin, and 6.3% of other ingredients.

The product thus obtained had a furfural content of 191 ppb, 4-VA content of 28.7 ppb, coloration degree of 0.23, and electric conductivity of less than 10 µS/cm. Also, the product contained calcium, potassium, magnesium, and sodium in respective amounts of about 0.5 ppm, about 0.07 ppm, about 0.09 ppm, and about 0.4 ppm.

Though the product is inferior to the particulate glycosyl hesperetins obtained in Examples 1 to 5, it has advantageously characteristic features compared to conventional products: It is significantly reduced in miscellaneous tastes and distinctly reduced in coloration and odor, and also the miscellaneous tastes are significantly reduced and the coloration and odor are effectively, distinctly decreased even after heated for 30 min under a relatively high temperature condition of 90 to 100° C. Accordingly, food products, cosmetics, pharmaceuticals such as susceptive diseases, quasi-drugs, chemicals, industrial materials and ingredients, feeds, baits, clothes, sundries including commodities, or plastic products, all of which, containing the product, are significantly reduced in miscellaneous tastes and distinctly reduced in coloration and odor as advantageous benefits, when kept or stored at a temperature within or below the above temperature range for several tens of minutes through several months, compared to those with conventional products. Similar to conventional products, the product can be advantageously used as a vitamin P-enriched agent, as well as a highly-safe natural anti-oxidant, stabilizer, quality-improving agent, preventive, therapeutic agent, or ultraviolet-absorbing agent in various compositions such as food products, luxury grocery items, cosmetics, pharmaceuticals such as susceptive diseases, quasi-drugs, chemicals, industrial materials and ingredients, feeds, baits, clothes, sundries including commodities, plastic products, etc.

Example 8

<Method for Reducing the Miscellaneous Tastes of Glycosyl-Hesperetin-Containing Product>

A particulate glycosyl hesperetin was obtained by adding sodium sulfite, sodium hyposulfite, potassium hyposulfite, or sodium pyrosulfite to the later described particulate glycosyl hesperetin, obtained in Example for Reference 1, in an amount of 0.03%, d.s.b., mixing the mixture to homogeneity, heating the resulting mixture, and then purifying the resultant.

This method is a quite simple technique of only adding any of the above reducing agents to the particulate glycosyl hesperetin obtained in Example for Reference 1, however, it has an advantage of significantly reducing the miscellaneous tastes inherent to conventional products. Since the particulate glycosyl hesperetin obtained by this method is not only significantly reduced in miscellaneous tastes but distinctly reduced in coloration and odor, the miscellaneous taste inducible by the product is significantly reduced, and the coloration and odor that are also inducible by the product are effectively and distinctly decreased even when incorporated into food products and then either treated by heating or stored in a solution form under heating conditions for a relatively long period of time.

Example 9

<Mixed Sweetener>

A liquid vitamin P-enriched mixed sweetener was obtained by subjecting 100 parts by mass of an isomerized sugar, two parts by mass of sucrose, and one part by mass of a particulate glycosyl hesperetin, obtained by the method in Example 1, to a 30-minute heat treatment at 80° C.

The product is a liquid vitamin P-enriched mixed sweetener that is effectively reduced in the miscellaneous tastes, coloration, and odor characteristic of conventional products. Accordingly, whenever food products are cooked with the product, unfavorable miscellaneous tastes, coloration, and odor inducible by the product should not be concerned, it does not deteriorate the taste, flavor, and color tone of food materials used as a merit.

Example 10

<Hard Candy>

A vitamin P-enriched hard candy was obtained by concentrating a solution of 20 parts by mass of water and 10 parts by mass of "TREHA", a registered trade mark for α,α-trehalose, commercialized by Hayashibara Co., Ltd., Okayama, Japan, in vacuo at 155° C. up to give a moisture content of about two percent or lower; cooling the concentrate up to 120° C.; mixing the resultant with 0.5 part by mass of citric acid, 0.01 part by mass of a particulate glycosyl hesperetin obtained by the method in Example 2, and an adequate amount of a lemon flavor; and shaping and packing the resulting mixture in conventional manner to obtain the captioned product.

Unlike hard candies prepared with conventional products, the product is effectively reduced in the miscellaneous tastes, coloration, and odor characteristic of such conventional hard candies, and thus it is a vitamin P-enriched hard candy free from deterioration of lemon flavor and transparency thereof.

Example 11

<Encapsulated Formulation>

An encapsulated formulation with a net weight of 150 mg per capsule was obtained by mixing to homogeneity 10 parts by mass of calcium acetate monohydrate, 50 parts by mass of magnesium L-lactate trihydrate, 57 parts by mass of maltose, 20 parts by mass of a particulate glycosyl hesperetin obtained by the method in Example 3, and 12 parts by mass of a γ-cyclodextrin inclusion compound containing 20% of eicosapentaenoic acid, subjecting the resulting mixture to a granulator, and encapsulating the resultant in a gelatin capsule in conventional manner.

Even after standing at ambient temperature or higher for a relatively long period of time, the product can be advantageously used, for example, as a high-quality blood cholesterol reducing agent, immuno-activator, or skin-beautifying agent as a prophylactic or therapeutic agent for susceptive diseases or a health-promoting food product, all of which are substantially free from increment or deterioration of miscellaneous tastes, coloration, or odor inducible by the product.

Example 12

<Bath Additive>

A bath additive was obtained by mixing 21 parts by mass of sodium DL-lactate, eight parts by mass of sodium pyruvate, five parts by mass of a particulate glycosyl hesperetin obtained by the method in Example 4, and adequate amounts of a colorant and a flavor.

The product is diluted with warm water in a bathtub by 100 to 10,000 folds. Even after a lapse of one hour or longer from the addition of the product to a circulating warm water in the bathtub, the product neither substantially increases nor changes coloration and odor inherent to the product, compared to those just after its addition to the warm water, as well as not deteriorating the fragrance of the flavor contained in the product, meaning that the product is a high-quality bath additive.

Example 13

<Milky Lotion>

A half part by mass of polyoxyethylene behenyl ether, one part by mass of polyoxyethylene sorbitol tetraoleate, one part by mass of glyceryl monostearate lipophilic, 0.5 part by mass of pyruvic acid, 0.5 part by mass of behenyl alcohol, one part by mass of avocado oil, one part by mass of a particulate glycosyl hesperetin obtained by the method in Example 1, and adequate amounts of vitamin E and an antiseptic were dissolved by beating in usual manner. To the resulting solution were added one part by mass of sodium L-lactate, five parts by mass of 1,3-butylene glycol, 0.1 part by mass of carboxyvinylpolymer, and 85.3 parts by mass of refined water, followed by emulsifying the mixture with a homogenizer, adding an adequate amount of a flavor to the homogenized product, and mixing the resultant to obtain a milky lotion.

Even after standing under ambient temperature or a condition of slightly higher temperature than that for a relatively long period of time, the product is a high quality milky lotion, which is substantially free from any increment or deterioration of miscellaneous tastes, coloration, and odor inducible by the product, as well as being free from deterioration of the fragrance of the incorporated flavor.

Example 14

<Vitamin-P-Enriched Agent>

To one part by mass of a particulate glycosyl hesperidin, obtained by the method in Example 4, were added one or more of sodium sulfite, sodium hyposulfite, potassium hyposulfite, and sodium pyrosulfite in a total amount of 0.0005 part by mass; and mixed to homogeneity to obtain 15 different types of vitamin-P-enriched agents as health food supplements.

Even after standing under ambient temperature or relatively higher temperature conditions for several tens of minutes to several months and then being added to beverages such as green tea, black tea, coffee, and cocoa before drinking, all the products are substantially free from any increment or deterioration of miscellaneous taste, coloration, and odor inducible by them, meaning that they are vitamin-P-enriched agents with improved storage stability and thermostability.

Example 15

<Food for Beauty>

Ten parts by mass of any one of the particulate glycosyl hesperetins obtained in Examples 1 to 7, three parts by mass of sucrose, one part by mass of maltitol, and 15 parts by mass of dextrin were mixed by stirring, and five-gram aliquots of the resulting mixture were placed in stick-type light-shielded and moisture-proof packaging containers to obtain eight different types of particulate foods for beauty of the present invention.

Since the products are effectively reduced in miscellaneous taste, coloration, and odor, they can be orally ingested daily without discomfort. They can be orally taken daily in such a manner of adding one or two packs of each of them in various beverages such as water, teas, black teas, and coffees, as well as other food products.

Example 16

<Food for Beauty>

Fifteen different types of liquid cosmetic foods according to the present invention were obtained by mixing with stirring two parts by mass of any one of the 15 different types of vitamin P-enriched agents obtained in Example 14, two parts by mass of maltose, 20 parts by mass of refined water, and an adequate amount of a pH-controlling agent; adjusting the resulting mixture to pH 7.2; subjecting the mixture to membrane filtration; and aseptically injecting the filtrate into aseptic containers to obtain 15 different types of liquid foods for beauty according to the present invention.

Since the products are reduced in miscellaneous tastes, coloration, and odor, they can be orally ingested without any discomfort. They can be orally taken daily in an amount of 50 to 200 mL/day to maintain the skin in healthy conditions.

Example for Reference 1

<Particulate Glycosyl Hesperetin>

A particulate glycosyl hesperetin was obtained similarly as in Example 1, except for not using sodium hyposulfite as a reducing agent used in the method for producing the particulate glycosyl hesperetin of Example 1, as a method for producing a conventional particulate glycosyl hesperetin. The particulate glycosyl hesperetin, obtained in this example, contained 77.0% of α-glucosyl hesperidin, 15.5% of hesperidin, and 7.5% of other ingredients.

The product had a furfural content of 310 ppb, 4-VA content of 40 ppb, coloration degree of 0.24, and electric conductivity of about 11 μS/cm. Also, the product contained calcium, potassium, magnesium, and sodium in respective amounts of about 3 ppm, about 0.2 ppm, about 0.4 ppm, and about 1 ppm.

The particulate glycosyl hesperetin thus obtained was dissolved in an adequate amount of water and tasted, revealing that it had miscellaneous tastes and coloration characteristic of conventional products and even had a strong unfavorable odor.

Accordingly, the glycosyl hesperetin, prepared without using any of the reducing agents used in practicing the present invention, was apparently inferior to the glycosyl hesperetin according to the present invention in terms of, at least, miscellaneous tastes, coloration, and odor.

INDUSTRIAL APPLICABILITY

The glycosyl hesperetin of the present invention, which is significantly reduced in miscellaneous taste and distinctly reduced in coloration and odor as compared to conventional products, can be stably provided on an industrial scale and at a relatively lower cost; and thus it is easily used without difficulty in the fields where conventional products could not be used or would be problematic due to their characteristic miscellaneous tastes along with or without coloration, as well as odor. Accordingly, the present invention will give a magnificent influence on the art and has a distinctly significant industrial applicability.

We claim:

1. A method for producing a glycosyl hesperetin composition, which comprises, as glycosyl hesperetin, α-glycosyl hesperidin and either or both of hesperidin and 7-O-β-glucosyl hesperetin in an amount of 90% or more by mass but less than 100% by mass, on a dry solid basis, wherein the content of furfural, measured on GC/MS analysis is less than 200 ppb, on a dry solid basis, the method comprising the steps of:
    (a) providing an aqueous solution comprising hesperidin and a partial starch hydrolyzate;
    (b) allowing a saccharide-transferring enzyme to act on the resulting aqueous solution to form glycosyl hesperetin; and
    (c) collecting the formed glycosyl hesperetin to obtain the glycosyl hesperetin composition,
    wherein one or more of the steps (a) to (c) are conducted in the presence of an inorganic reducing agent.

2. The method of claim 1, wherein said saccharide-transferring enzyme used in the step (b) is one or more members selected from the group consisting of cyclomaltodextrin glucanotransferase, a-glucosidase, and a-amylase.

3. The method of claim 1, wherein the enzymatic reaction solution obtained in the step (b) is subjected to the action of glucoamylase and/or a-L-rhamnosidase.

4. The method of claim 1, wherein said inorganic reducing agent is a sulfite.

* * * * *

UNITED STATES PATENT AND TRADEMARK OFFICE
CERTIFICATE OF CORRECTION

PATENT NO. : 10,703,773 B2
APPLICATION NO. : 15/122708
DATED : July 7, 2020
INVENTOR(S) : Mitsuyuki Kambe et al.

Page 1 of 1

It is certified that error appears in the above-identified patent and that said Letters Patent is hereby corrected as shown below:

In the Claims

At Claim 2, Column 42, Line 49, delete "a-glucosidase, and a-amylase." and insert --α-glucosidase, and α-amylase.--

At Claim 3, Column 42, Line 52, delete "a-L-rhamnosidase." and insert --α-L-rhamnosidase.--

Signed and Sealed this
Seventeenth Day of November, 2020

Andrei Iancu
*Director of the United States Patent and Trademark Office*